United States Patent [19]

Scinto et al.

[11] Patent Number: 5,704,369

[45] Date of Patent: Jan. 6, 1998

[54] NON-INVASIVE METHOD FOR DIAGNOSING ALZEHEIMER'S DISEASE IN A PATIENT

[75] Inventors: Leonard Scinto, Cambridge; Kirk R. Daffner, Newton, both of Mass.

[73] Assignee: Beth Israel Hospital Association, Inc., Boston, Mass.

[21] Appl. No.: 532,319

[22] Filed: Sep. 22, 1995

Related U.S. Application Data

[63] Continuation-in-part of Ser. No. 447,630, May 23, 1995, Pat. No. 5,617,872, which is a continuation-in-part of Ser. No. 279,795, filed as PCT/US95/09389, Jul. 24, 1995, abandoned.

[51] Int. Cl.$^6$ .................................................. A61B 13/00
[52] U.S. Cl. .............................................................. 128/745
[58] Field of Search ................................. 128/731, 745, 128/897, 898; 351/205, 221

[56] References Cited

U.S. PATENT DOCUMENTS

| | | | |
|---|---|---|---|
| 4,755,043 | 7/1988 | Carter | 351/205 |
| 4,850,691 | 7/1989 | Gardner | 351/221 |
| 5,141,305 | 8/1992 | Young | 351/243 |
| 5,187,506 | 2/1993 | Carter | 351/223 |
| 5,297,562 | 3/1994 | Potter | 128/898 |
| 5,305,764 | 4/1994 | Yamada et al. | 128/745 |

OTHER PUBLICATIONS

Amaducci, et al., "Risk factors for Clinically Diagnosed Alzheimer's Disease: A Case–control Study of an Italian Population," *Neurology* 36:922–931 (1986).

Brion, et al., "Senile Dementia of the Alzheimer Type: Morphological and Immunocytochemical Studies," in *Senile Dementia of the Alzheimer Type*, pp. 164–174 (1985).

Civil, et al., "Degenerative Dementias," in *Dimentia*, pp. 167–176 (1987).

Cork, et al., "Phosphorylated Neurofilament Antigens in Neurofibrillary Tangles in Alzeheimer's Disease," *Journal of Neuropathol. and Exp. Neurol.* 45:56–64 (1986).

DeSauvage, et al., "A Novel mRNA of the A4 Amyloid Precursor Gene Coding for a Possibly Secreted Protein," *Science* 245:651–653 (1989).

DeSouza, et al., "Reciprocal Changes in Corticotropin-releasing Factor (CRF)-like Immunoreactivity and CRF Receptors in Cerebral Cortex of Alzheimer's Disease," *Nature* 319:593–595 (1986).

Dyrks, et al., "Identification, Transmembrane Orientation and Biogenesis of the Amyloid A4 Precursor of Alzheimer's Disease," *The EMBO Journal* 7:949–957 (1988).

(List continued on next page.)

*Primary Examiner*—Max Hindenburg
*Attorney, Agent, or Firm*—Michael A. Sanzo; Vinson & Elkins

[57] ABSTRACT

The present invention provides non-invasive methods for diagnosing Alzheimer's disease in a living human subject. One method employs a non-invasive automated apparatus which can continuously monitor pupil diameter size over time; repetitively measure pupil diameter size over time for a pre-chosen duration ranging from about less than 1 second to about 5 minutes; and cumulatively record size information as it is obtained over time. A second method employs an apparatus which can repetitively measure pupil constriction velocity for a pre-chosen duration both before and after stimulation by visible light. Both methods require the administration of at least one neural transmitter mediator to a targeted eye of the living subject in an amount insufficient to cause marked changes in pupil diameter size over time in a person who is not afflicted with Alzheimer's disease. The marked hypersensitivity of an Alzheimer's dementia patient to the administered neural transmitter mediator serves as the means for identifying individuals afflicted with Alzheimer's disease.

19 Claims, 6 Drawing Sheets

OTHER PUBLICATIONS

Francis, et al., "Neurochemical Studies of Early-Onset Alzheimer's Disease," *New England Journal of Medicine* 313:7–11 (1985).

Goldgaber, et al., "Characterization and Chromosomal Localization of a cDNA Encoding Brain Amyloid of Alzheimer's Disease," *Science* 235:877–880 (1987).

Gonatas, et al., "The Contribution of Altered Syapses in the Senile Plaque: An Electron Microscopic Study in Alzheimer's Dementia," *Journal of Neuropath. & Exp. Neurol.* 26:25–39 (1967).

Idiaquez, et al., ":Cholinergic Supersensitivity of the Iris in Alzheimer's Disease,"*Journal of Neurology, Neurosurgery, and Psychiatry*, 57:1544–1545 (1994).

Kemper, "Neuroanatomical and Neuropathological Changes in Normal Aging and in Dementia," in *Clinical Neurology of Aging*, pp. 9–52 (1984).

Kidd, "Alzheimer's Disease—An Electron Microscopical Study," *Brain* 897:307–320 (1964).

Kitaguchi, et al., "Novel Precursor of Alzheimer's Disease Amylolid Protein Shows Protease Inhibitory Activity," *Nature* 331:530–532 (1988).

Koo, et al., "The Neurobiology of Dementia," in *Dementia*, pp. 55–67 (1987).

Masters, et al., "Neuronal Origin of a Cerebral Amyloid: Neurofibrillary Tangles of Alzheimer's Disease Contain the Same Protein as the Amyloid of Plaque Cores and Blood Vessels," *The EMBO Journal* 4:2757–2763 (1985).

Nieto, et al., "Altered Levels of Microtubule Proteins in Brains of Alzheimer's Disease Patients," *Acta Neuropathol.* 78:47–51 (1989).

Paykel, et al., "Incidence of Dementia in a Population Older Than 75 Years in the United Kingdom," *Arch. Gen. Psychiatry* 51:325–332 (1994).

Ponte, et al., "A New A4 Amyloid mRNA Contains a Domain Homologous to Serine Proteinase Inhibitors," *Nature* 331:525–527 (1988).

Rafalowska, et al., "Laminar Distribution of Neuritic Plaques in Normal Aging, Alzheimer's Disease and Down's Syndrome," *Acta Neuropathol.* 77:21–25 (1988).

Roher, et al., "Isolation and Chemical Characterization of Alzheimer's Disease Paired Helical Filament Cytoskeletons: Differentiation from Amyloid Plaque Core Protein," *Journal of Cell Biology* 107:2703–2716 (1988).

Sacks, et al., "People with Down's Syndrome Can be Distinguished on the Basis of Cholinergic Dysfunction," *Journal of Neurology, Neurosurgery, and Psychiatry* 52:1294–1295 (1989).

Scinto, et al., "A Potential Noninvasive Neurobiological Test for Alzheimer's Disease," *Science* 266:1051–1054 (1994).

St. George-Hyslop, et al., "The Genetic Defect Causing Familial Alzheimer's Disease Maps on Chromosome 21," *Science* 235:885–890 (1987).

Tanzi, et al., "Amyloid $\beta$ Protein Gene: cDNA, mRNA Distribution, and Genetic Linkage Near the Alzheimer Locus," *Science* 235:880–884 (1987).

Tanzi, et al., "Protease Inhibitor Domain Encoded by an Amyloid Protein Precursor mRNA Associated with Alzheimer's Disease," *Nature* 331:528–530 (1988).

Weidemann, et al., "Identification, Biogenesis, and Localization of Precursors of Alzheimer's Disease A4 Amyloid Protein," *Cell* 57:115–126 (1989).

Whitehouse, et al., "Alzheimer's Disease and Senile Dementia: Loss of Neutrons in the Basal Forebrain," *Science* 215:1237–1239 (1982).

Whitehouse, et al., "Reductions in Corticotropin Releasing Factor-like Immunoreactivity in Cerebral Cortex in Alzheimer's Disease, Parkinsons's Disease, and Progressive Supranuclear Palsy," *Neurology* 37:905–909 (1987).

Wisniewski, et al., "Comparison of Four Staining Methods on the Detection of Neuritic Plaques," *Acta Neuropathol.* 78:22–27 (1989).

Wisniewski, et al., "Neurofibrillary Tangles of Paired Helical Filaments," *Journal of the Neurological Sciences* 27:173–181 (1976).

Technical Manual from Applied Science Laboratories regarding Series 4000 Systems (1992).

Technical Manual from Applied Science Laboratories regarding Pupilscan/Pupilscreen, Addendum for Version 2.09, Jan. 1993.

NON-INVASIVE METHOD FOR DIAGNOSING ALZHEIMER'S DISEASE IN A PATIENT

CROSS REFERENCE TO RELATED APPLICATIONS

The present application is a continuation of PCT/US95/09389, with an international filing date of Jul. 24, 1995, which is a continuation-in-part of U.S. application Ser. No. 08/447,630, filed May 23, 1995 (now U.S. Pat. No. 5,617,872) which is a CIP of U.S. application Ser. No. 08/279,795, filed Jul. 25, 1994 (now abandoned).

FIELD OF THE INVENTION

The present invention is concerned with non-invasive methods for the diagnosis of Alzheimer's Disease in a living human patient and is particularly directed to using changes in pupillary characteristics caused by the application of neural transmitter agonists or antagonists to Alzheimer's Disease patients as a means of diagnosis.

BACKGROUND OF THE INVENTION

Alzheimer's Disease ("AD") is a dementing disorder characterized by progressive impairments in memory and cognition. It typically occurs in later life; and is associated with a multiplicity of structural, chemical and functional abnormalities involving brain regions concerned with cognition and memory. This form of dementia was first reported by Alois Alzheimer in 1907 when he described a disease of the cerebral cortex in a 51-year-old woman suffering from an inexorably progressive dementing disorder. Although other forms of dementia had been well characterized at the time of Alzheimer's clinical report, his patient was clinically and pathologically unusual, because of her relatively young age and the presence of the then newly described intra-cellular inclusions which have subsequently come to be known as neurofibrillary tangles ("NFTs"). In recognition of this unique combination of clinical and pathological features, the term "Alzheimer's Disease" subsequently came into common usage.

Today, Alzheimer's Disease is considered to be one of the forthcoming scourges of the 21st century. This is due in major part to the aging of the population in concert with data indicating a marked increase in the incidence of dementia with advancing age. Epidemiologic studies suggest that the dementia presently occurs in up to 10% of individuals over the age of 65 and it is estimated that in the United States alone, as many as 4 million individuals may be affected with Alzheimer's Disease. The cost of caring for such individuals is well over 80 billion dollars annually and increasing rapidly.

Since the recognition of this form of dementia as a specific disorder, many different neurobiologic approaches have been undertaken to studying and understanding the nature and the mechanism of action for Alzheimer's Disease, with a view to possible future therapeutic treatments and/or prevention. Representative of the range and diversity of these many neurobiologic approaches are those listed within Table 1 below.

TABLE 1

Neurobiologic Approaches to the Study of Alzheimer's Disease*

| Biologic Measures | Methods | Examples |
|---|---|---|
| Brain metabolism | In vivo imaging studies | Reduced glucose utilization in neocortex, esp. parietal and temporal areas |
| Histology of brain | Histochemistry, immunocytochemistry | /A4 immunoreactive plaques in neocortex and hippocampus |
| Quantitation of pathology | Morphometric methods | Reduced number of neurons in basal forebrain cholinergic system |
| Neuron size and shape | Golgi Stains | Abnormal dendritic arborizations |
| Ultrastructure | Electron microscopy, immunocytochemistry | PHF in NFT and /A4 fibrils in plaques |
| Transmitters and enzymes | Assays of markers | Reduced levels of ChAT, somatostatin, and CRF in cortex |
| Receptors | Binding Assays in vitro autoradiography | Reduced cortical somatostatin receptors and increased cortical CRF receptors |
| Proteins in abnormal organelles | Purification of constituents, analyses of proteins and other components, immunocytochemistry freeze-fracture/deep-etch | Decoration of PHF with antineurofilament and antitau antibodies; tubulinlike immunoreactivity in GVD; actin in Hirano bodies; /A4 in plaque cores and congo philic angiopathy |
| Proteins and their modifications | Immunoblots, immunocytochemistry, in vitro incorporation of amino acids | Phosphorylated 200-kD neurofilament A68 and tau associated with NFT; aberrant processing APP and PrP amyloid |
| RNAs | Hybridization on gels and in situ; measurements of mRNAs and enzymes acting on RNAs | Reduced mRNA in some cells; PrP and APP mRNA present in neurons |
| Genes | Recombinant DNA technology | Anonymous marker on chromosome 21 linked to familial AD; APP gene localized to chromosome 21 |

ABBREVIATIONS
AD      Alzheimer's disease
/A4     -amyloid protein
CHAT   choline acetyltransferase
CRF    corticotropin-releasing factor
GVD    granulovacuolar degeneration
kD      kilodalton(s)
mRNA  messenger ribonucleic acid(s)
NFT    neurofibrillary tangle(s)
PHF    paired helical filament(s)
PrP     prion protein
*Source:  DEMENTIA (Peter J. Whitehouse, Ed.), F. A. Davis Co., Philadelphia, 1993, Chapter 3, pp. 56–57.

In addition, a great many research studies and clinical investigations have been undertaken to study the structural deficiencies, chemical changes, and functional abnormalities both within the brain and within different populations of nerve cells. The depth of such investigations and studies are represented by the following publications: *Dementia*, (J. Whitehouse, Ed.), F. A. Davis Company, Philadelphia, 1993; Paykel, et al., *Arch. Gen. Psychiat.*, 51:325–332 (1994); Amaducci, et al., *Neurology*, 36:922–931 (1986); McKhann, et al., *Neurology* 34:939–944 (1984), Heston et al., *Arch. Gen. Psychiatry* 38:1085–1090 (1981); *Aging of the Brain* (Gispen and Traber, editors), Elsevier Science Publishers, Amsterdam, 1983, pages 275–282; Heyman et al., *Ann.*

Neurol 15:335–341 (1984); Brayne C. and P. Calloway, Lancet 1:1265–1267 (1988); Roth et al., Br. J. Psychiatry 149:698–709 (1986); Medical Research Council, Report from the NRC Alzheimer's Disease Workshop, London, England, 1987; Morris et al., Neurology 41:469–478 (1991); Alzheimer's Disease: Senile Dimentia and Related Disorders (Katzman, T. D. and R. L. Bick, editors), Raven Press, New York, 1994, pages 47–51; and the references cited within each of these publications.

In spite of the many research investigations and diverse studies undertaken to date, present clinical evaluations still cannot establish an unequivocal diagnosis of Alzheimer's Disease. To the contrary, the only presently known means for positively proving and demonstrating Alzheimer's Disease in a patient can only be achieved by a brain biopsy or a postmortem examination to assess and determine the presence of neurofibrillary tangles (NFT) and senile (amyloid) plaques in brain tissue. These criteria for the definite diagnosis of Alzheimer's Disease are met only by histologic evidence.

Instead, a set of criteria for the diagnosis of probable Alzheimer's Disease have been described and include: (1) the presence of a dementia syndrome with defects in two or more areas of cognition; (2) progressive worsening of memory and other cognitive function over time; (3) a relatively intact level of consciousness; (4) age at disease onset at a time between 40 and 90 years of age; and (5) the specific absence of any other systemic or central nervous system process that could account for the progressive cognitive deterioration in the individual.

In addition, the probability of an accurate diagnosis in the living patient is augmented by laboratory examinations (such as VDRL and TFT) and by imaging studies (such as computed tomography and magnetic resonance imaging). Such laboratory examinations and/or imaging studies demonstrate the existence and effects of other causes of dementia (such as subdural hematoma, intracranial tumors, infection and brain infarction) and disclose results which are consistent with but are not themselves diagnostic of Alzheimer's Disease. Nevertheless, present clinical diagnoses are wrong in as many as 55% of cases. Thus, there is no sound basis or reliable test methodology at all today for the diagnosis of definite Alzheimer's Disease other than the microscopic examination of histologic evidence from brain biopsy or autopsy material. Instead, the best clinical diagnosis available to date is only a presumptive determination based on criteria which are evaluations of cognitive and neurological functions for that patient.

It is therefore overwhelmingly clear that there has been and remains today a long standing need for an accurate method to diagnose Alzheimer's Disease clinically in a living human subject with substantial certainty and reliability. In addition, were such a diagnostic methodology also able to be non-invasive, rapid in time required for performance, and precise via the accumulation of large quantities of empirical data, such a diagnostic methodology would be recognized by physicians and laymen alike as being a major advance and substantial improvement in this field.

The mydriatic response to eyedrops of the anticholinergic agent tropicamide at very low concentration (0.01%) has been studied in patients with Down's syndrome, with a report that, in comparison with normal subjects, Down's syndrome patients had responses three times greater than normal patients. Sacks, et al., J. Neurology, Neurosurgery, and Psychiatry, 1989:52, 1294–1295. Sacks, et al. state that since patients with Alzheimer's disease appear to show behavioral and cognitive sensitivity to hyoscine, the eyedrop test could be used to distinguish people with Alzheimer's disease from patients with other forms of dementia, allowing for a definitive diagnosis in a living patient. U.S. Pat. No. 5,297,562 states that Alzheimer's disease can be diagnosed before symptoms of dementia occur by determining whether a patient is mosaic for trisomy 21, including by measuring certain characteristics known to be associated with Down's syndrome. Among the characteristics listed by Potter are pupil dilation, with citation to Sacks, et al.

U.S. patent application Ser. No. 08/109,746, filed Aug. 20, 1993, apparently relates to the use of a mydriadic response to diagnose Alzheimer's disease in a patient, including methodologies that use an untreated eye as a control for determining the mydriatic response in a treated eye.

SUMMARY OF THE INVENTION

The present invention provides non-invasive methods for diagnosing Alzheimer's Disease in a patient, i.e., living human subject. In particular the present invention provides:

A non-invasive method for diagnosing the presence or absence of Alzheimer's disease in a living subject which comprises:

administering to one of said subject's eyes at least one neural transmitter mediator in an amount insufficient to cause a significant pupil constriction or dilation if said subject is not afflicted with Alzheimer's disease, repetitively and episodically measuring pupil diameter in said treated eye during at least a part of the time said neural transmitter mediator or mediators would have an observable effect on pupil diameter in a subject afflicted with Alzheimer's disease, and diagnosing the presence or absence of Alzheimer's disease in said subject based on the presence or absence of Alzheimer-characteristic pupil diameter changes from a baseline pupil diameter established for said treated eye or Alzheimer's-characteristic pupil diameter rates of change calculated from said pupil diameter change measurements.

In addition to the above diagnostic method, the present invention further relates to a method, as described above, that additionally comprises:

photostimulating said subject's treated eye with one or more episodes of visible light to induce pupillary constriction, such that said episodic measurements of pupil diameter occur during the pupil contriction in response to said photostimulation, said pupil diameter measurements being thereafter used to determine the rate of change of pupil constriction (pupil constriction velocity).

In its most useful embodiment, the present invention is practiced in a manner in which said repetitive measurements occur at a high frequency, i.e. at least 50 Hertz, over a duration sufficient to provide a statistically meaningful measure of the pupil diameter dynamic used as the diagnostic determinant. Ordinarily, therefore, the diagnostic method of this invention will assess actual pupil diameter from at least 1000 separate measurements of pupil diameter, or at least 100 separate measurements each time photostimulated constriction velocity is measured. Preferably, each of these high-frequency measurements is repeated multiple times, extending at least up to the time of maximum expected sensitivity of the subject to the mediator. Thus, ordinarily, three to six post-administration episodes of high frequency measurement would be undertaken, in addition to one or more baseline measurements.

As noted above, the changes in pupil diameter (e.g., maximal change in pupil diameter using the post-administration high-frequency measures compared to the high-frequency baseline measure) or photostimulated pupil contriction velocity are then matched with Alzheimer's-characteristic measures for these parameters to assess the likelihood that the subject is afflicted with Alzheimer's disease. These Alzheimer's-characteristic values are readily and empirically determined since Alzheimer's patients typically exhibit highly statistically significant different responses when the high-frequency, multiple-episode measures are undertaken. For example, the separation of dynamic values as between normal patients and Alzheimer's-afflicted patients is normally at least 10% and typically at least 15% or greater following administration of 0.01% tropicamide, allowing for a direct statistical correlation between the pupil dynamic change and the likelihood (probability) that subject has Alzheimer's disease.

In its actual operation, the invention includes a diagnostic method comprising the steps of:

- providing a non-invasive automated apparatus which can continuously monitor pupil diameter size over time, repetitively measure pupil diameter size over time for a prechosen duration ranging from about less than 1 second to about 5 minutes, and cumulatively record such monitored and measured pupil diameter size information as is obtained over time;
- identifying one eye in the living human subject as a targeted eye;
- using said non-invasive automated apparatus on a first measurement occasion to continuously monitor, repetitively measure, and cumulatively record the pupil diameter size of said targeted eye in the living human subject over the prechosen duration to provide primary informational data of pupil diameter size for said targeted eye;
- administering at least one neural transmitter mediator to said targeted eye of the living human subject in an amount insufficient to cause marked changes in pupil diameter over time in a person not afflicted with Alzheimer's disease, said neural transmitter mediator being selected from the group consisting of cholinergic and adrenergic antagonists and agonists;
- waiting a predetermined interval of time sufficient for said administered neural transmitter mediator to act upon said targeted eye; then
- using non-invasive automated apparatus on at least a second measurement occasion to continuously monitor, repetitively measure, and cumulatively record the pupil diameter size of said targeted eye in the living human subject over the prechosen duration to provide at least secondary informational data of pupil diameter size for said targeted eye after being acted upon by said administered neural transmitter mediator; and
- determining at least one parameter selected from the group consisting of pupil diameter dilation, pupil diameter constriction, and the rate of pupil diameter change for said targeted eye as occurred over said time interval by comparing said primary informational data with at least said secondary informational data, whereby a marked increase in pupil diameter size, or a marked decrease in pupil diameter size, or rapid rate of pupil diameter change for said targeted eye diagnostically establishes the living human subject as being afflicted with Alzheimer's disease.

Alternatively, the invention can be practiced using photostimulation to measure pupil constriction velocity in the following manner:

providing non-invasive apparatus means for
  (a) introducing photostimulating visible light of predetermined wavelength and intensity to the eye on-demand sufficient to cause a constriction of the pupil, and
  (b) determining the velocity of pupil constriction caused by said introduced photostimulating visible light;

identifying one eye in the living human subject as a targeted eye;

administering at least one neural transmitter mediator to said targeted eye of the living human subject in an amount insufficient to cause a marked change in pupillary dynamic response in a person not afflicted with Alzheimer's disease, said neural transmitter mediator being selected from the group consisting of cholinergic antagonists and agonists;

waiting a predetermined interval of time for said administered neural transmitter mediator to act upon said targeted eye; then introducing photostimulating visible light of predetermined wavelength and intensity to the targeted eye sufficient to cause a constriction of the pupil using said non-invasive apparatus means; and determining pupil constriction velocity for said photostimulated targeted eye using said non-invasive apparatus means, a marked decrease in pupil constriction velocity for said targeted eye with respect to a pre-established normative standard diagnostically establishing that living human subject as being afflicted with Alzheimer's disease.

BRIEF DESCRIPTION OF THE FIGURES

The present invention can be more easily and completely understood when taken in conjunction with the accompanying in which.

DEFINITIONS

Figure 1:
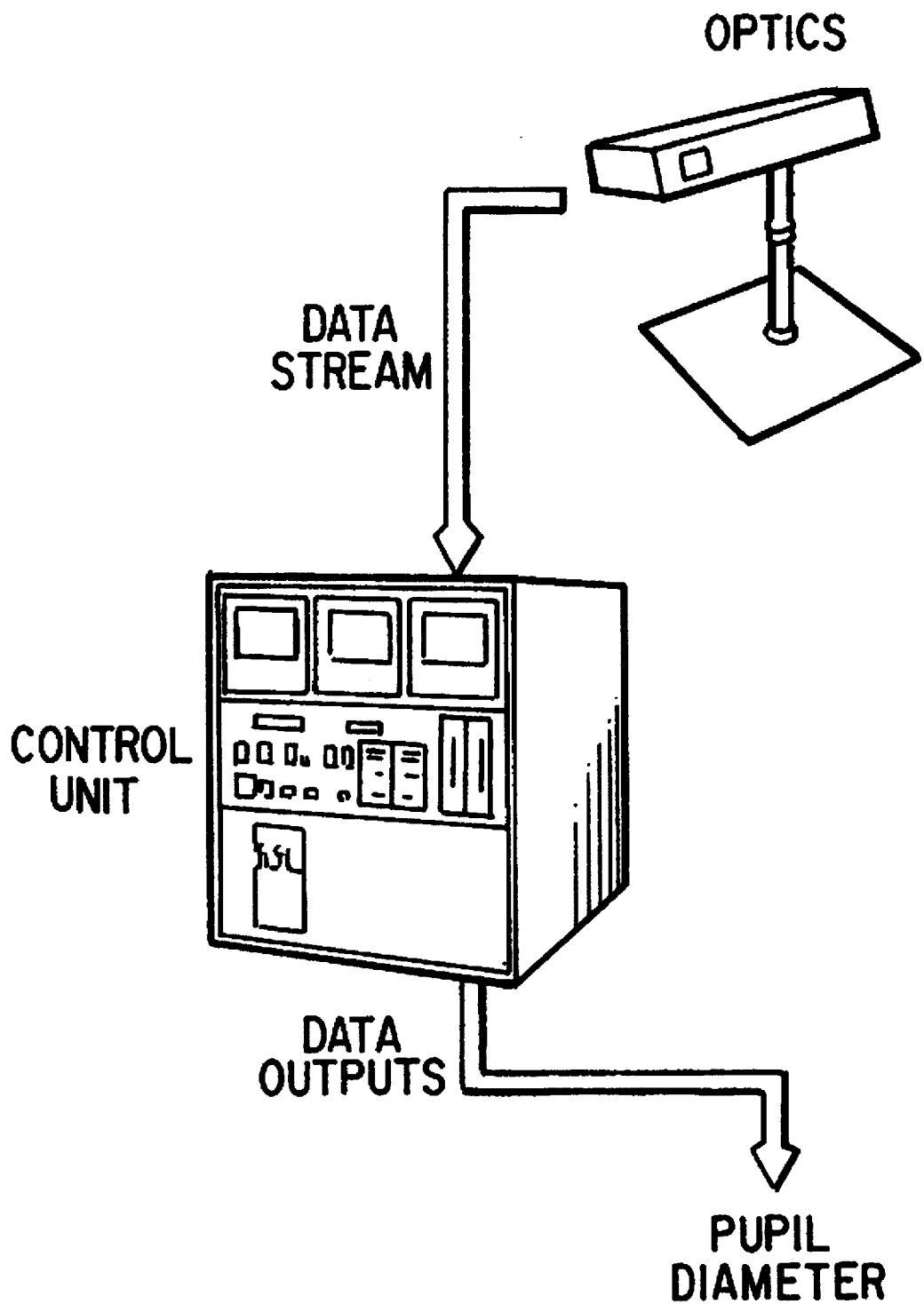
FIG. 1 is a schematic illustration of the series 4000 measurement apparatus as a system.
Figure 2:
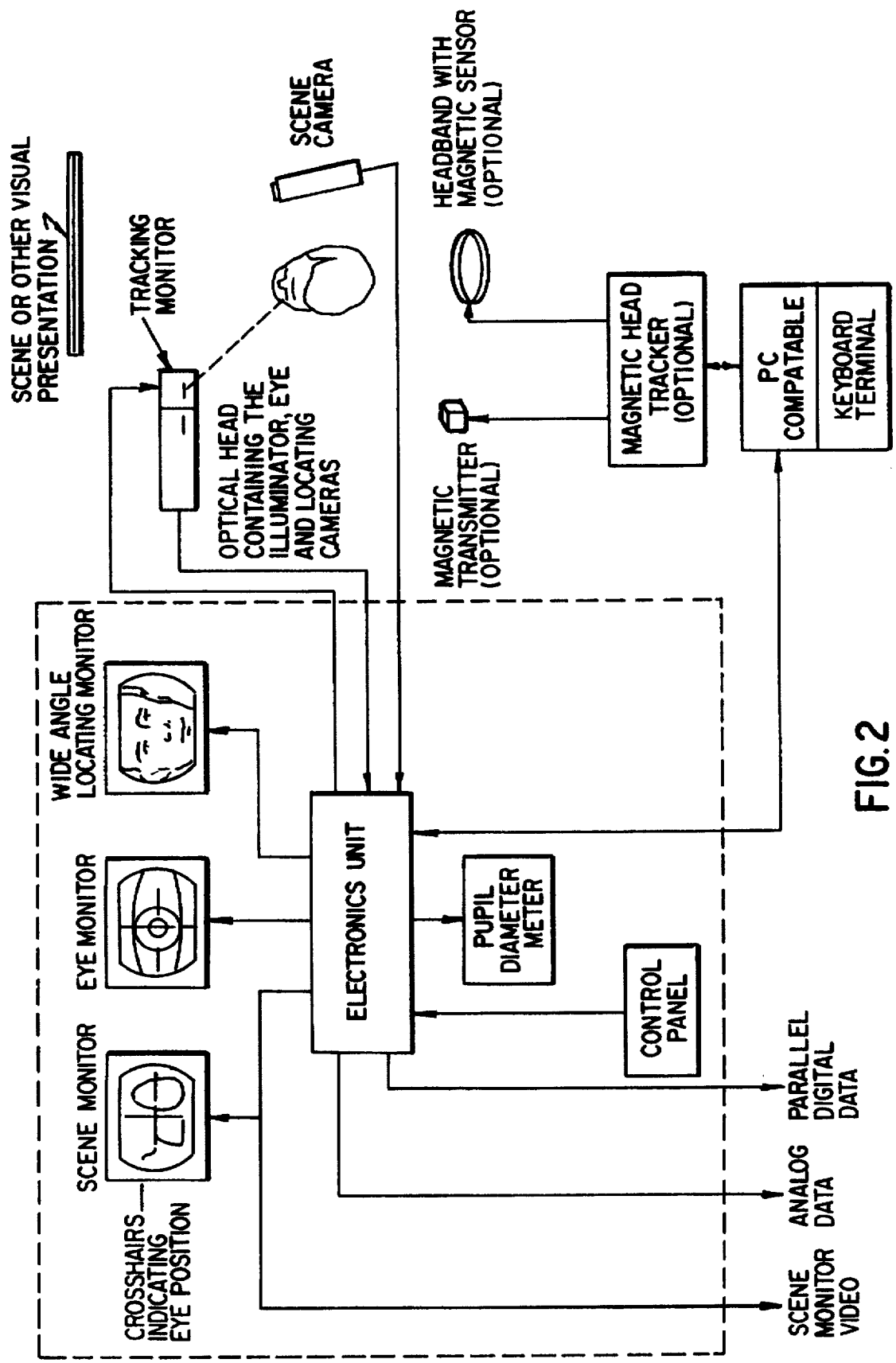
FIG. 2 is a schematic illustration of the optics and the series 4000 measurement apparatus as an integrated system.

In order to avoid ambiguity in terminology as well as to provide a clear and precise understanding of the scope of the present methodology, a set of specific terms and explicit definitions are given below. These words and their meanings will be employed repeatedly and routinely in this disclosure and the stated definitions are to be accepted as written and as part of the general lexicon and vocabulary in this art.

Cholinergic: A term pertaining to the neural transmitter acetylcholine. The term is particularly used to designate nerve fibers that release acetylcholine at their terminals, or the physiological effects produced by the stimulation of these nerve fibers, or the acetylcholine receptors on the post synaptic membrane, or chemical agents and drugs that imitate the effects of acetylcholine.

Adrenergic: A term designating activation by, characteristic of, or a secreting of the neural transmitter epinephrine or substances with similar epinephrine-like activity. The term is also used to refer to those postganglionic sympathetic nerve fibers that liberate norepinephrine in response to a nerve impulse; and is typically used to identify an agent that produces such an effect.

Mydriasis: Dilation of the pupil.

Mydriatic agent: A compound or substance which initiates, induces, promotes or causes pupil dilation.

Miosis: Constriction of the pupil.

Miotic agent: A compound or substance which initiates, induces, promotes, or causes pupil constriction.

Neural Transmitter (also Neurotransmitter and Synaptic Transmitter): A compound or substance that serves to transmit a nerve impulse between cells at a synapse or a neuromuscular junction. Such compounds include but are not limited to acetylcholine, epinephrine, norepinephrine, dopamine, serotonin, γ-aminobutyric acid, glycine, and glutamate.

Constriction Velocity: The average rate of change in pupil diameter expressed in mm/sec over a given interval of time from initial size to maximal constricted size of pupil.

Re-dilation velocity: The rate of recovery expressed as mm/sec to maximal resting pupil diameter after stimulation by light.

Endogenous substance: A compound or composition developing or originating within the person or arising from causes within the person's body.

Exogenous substance: A compound or composition synthesize, found, or originating outside the person's body.

Photostimulation (visible light stimulation): the purposeful introduction of visible light energy to the eye of a living subject.

Light energy (photoenergy): Electromagnetic radiation of any wavelength including infrared, visible and ultraviolet wavelengths.

Agonist: A compound or substance that imitates, mimics, or acts in a manner similar to the activity or function of a specified tissue, composition or agent.

Antagonist: A compound or substance that blocks the activity or function of a specified tissue, composition or agent.

Mediator: A compound, composition, agent or substance that influences, effects, intervenes, contradicts, mitigates, modifies, promotes, or is involved with an activity or function in a specified manner.

Velocity: The rate of change of size or rate of displacement typically expressed in unites (e.g., millimeters per second). Velocity is a vector quantity and a complete specification which states both the direction as well as the magnitude of change.

DETAILED DESCRIPTION OF THE INVENTION

The present invention is directed to non-invasive methods for diagnosing Alzheimer's disease in a living human subject. As will be described in detail below, these diagnostic methods take advantage of a new recognition that some aspects of the typical Alzheimer Disease patient's autonomic nervous system are hypersensitive to neural transmitter mediators administered specifically to the eye. In one method, measurements are made of changes in pupil diameter in response to neural transmitter mediators (cholinergic or adrenergic agonists and antagonists) when such mediators are applied at concentrations known to be too low to significantly affect pupil diameter in normal individuals.

In an alternative method, precise measurements are made of pupil constriction velocity in response to stimulation by a predetermined intensity and duration of visible light energy. The method utilizes differences in pupillary dynamic response to stimulation by a known quantity of light between Alzheimer's patients and cognitively intact persons to such pharmacologically active agents as an empirical basis and standard for accurately, positively and definitely diagnosing Alzheimer's dementia.

When performed in accordance with the prescribed manipulative steps, the present diagnostic methods provide many major benefits and multiple advantages which were not known or available previously. These include the following:

1. The present diagnostic methods are relatively non-invasive. The methodology utilizes automated equipment which can repetitively measure pupil diameter size changes over time and cumulatively record such data as it is obtained or which can accurately monitor pupil constriction velocity in response to light stimulation. The data so obtained can then be mathematically analyzed to provide a quantitative clinical result for comparison with an established numerical standard range of normal and abnormal values. In this manner, a definite, unambiguous, and reliable determination can be made as to whether or not that living human subject is afflicted with Alzheimer's Disease.

2. The use of automated equipment to monitor and record changes in pupil diameter size and pupillary responses provides a large quantum of empirical data which can be used for making a clinical diagnosis. The automated equipment is able to observe and measure pupil diameter size and constriction velocity quickly, accurately, and repetitively. For example, one of the devices described herein will provide 50 to 60 measurements per second for any desired duration of time. If the duration of measurement were extended for about 30 seconds, this would yield as many as 1,800 individual determinations. While the duration of pupil diameter measurements may vary considerably, there will be in each instance a quantity of raw data which far exceeds that reasonably obtainable using non-automated methods. This improves the accuracy and reliability of measurements.

3. The diagnostic methodology as a whole makes minimal demands upon the patient; does not involve physical exercise or fatiguing manipulations; and avoids the use of systemic medication. Instead, the present methods rely upon the use of dilute concentrations of neural transmitter mediators such as cholinergic antagonists and agonists and adrenergic antagonists and agonists. These neural transmitter mediators are administered to test subjects at concentrations which do not substantially influence pupillary responses in cognitively intact individuals. Accordingly, there is little or no probability that the diagnostic examination process will cause undesirable side effects.

4. The present diagnostic methods may be performed relatively easily and can be completed within about an hour. The diagnostic data are then generated as quickly as the central processing unit of the automated apparatus can operate; and the results appear in printed form or in visual form on a monitor and/or may be transferred to a remote reference facility for final analysis as is most desired or required under the use circumstances.

5. The diagnostic methods employ a pharmacological manipulation of the pupil of the eye. In one preferred method, a neurotransmitter mediator (cholinergic or adrenergic antagonist or agonist) is applied to one targeted eye of an individual being tested and his pupillary response (percent change over baseline or rate of change) is compared to norms established for a population of, preferably, age-matched, cognitively intact individuals. A significant difference from the established norm in the pupillary response of such an individual serves to diagnose Alzheimer's disease.

In a second preferred method, a cholinergic antagonist is applied to a subject's eye and the constriction velocity of his pupil in response to light stimulation is compared to the constriction velocity of normal individuals. Again, it is preferred that subjects be compared to an age matched normal population. A significant difference in constriction velocity would be indicative of Alzheimer's disease.

An alternative and less desirable method uses one eye of the individual as the targeted eye for treatment with neural mediators while the other eye is employed as an untreated control. In this manner, the difference in pupillary response is thus measured between the two eyes of the same living subject.

6. The present diagnostic methodology can be performed and practiced in several different modes. These procedures include measuring pupil diameter dilation; pupil diameter constriction; the rate of pupil diameter changes; and photostimulation-induced pupil velocity contriction.

The scientific basis for the present diagnostic methods is the recognition that persons afflicted with Alzheimer's dementia are uniquely hypersensitive to the pharmacological effects of neural transmitter mediators, particularly those administered topically to the eye. The existence of such hypersensitivity, however, is not only an intrinsic part of the disease process but also can be intentionally manipulated pharmacologically in the person afflicted with Alzheimer's Disease. Thus, the underlying principles for the present invention are first, that this unique hypersensitive state exists and manifests itself in the autonomic nervous system of the Alzheimer's patient; and second, that this hypersensitive state will manifest itself as an abnormal response to pharmacologically active antagonists and agonists in a distinctive manner which can be utilized for diagnostic purposes.

The present disclosure provides, for the first time, an empirical showing that hypersensitivity to neural transmitter mediators is specifically present in those neurons and nerve cell bodies which innervate the iris muscle of the eye. Thus, the administration of a neural transmitter mediator or modular (such as cholinergic or adrenergic antagonists or agonists) in a concentration which is generally insufficient to cause a marked or noticeable dilation or contraction of pupil diameter size in a cognitively intact individual—will nevertheless cause a change and marked alteration in pupil diameter size (dilation or contraction) in the person afflicted with Alzheimer's Disease.

Thus, the underlying principle of the present methods is that an intrinsic part of the Alzheimer's disease process is hypersensitivity to neural transmitters affecting the pupil; and the concomitant demonstration that pharmacologically active mediators can be employed to manipulate this disease condition and to yield a hypersensitive pupillary response. The present invention proves that these circumstances exist within the Alzheimer's population generally and thus may properly serve as a basis for making a differential diagnosis and determination by which to identify the presence of Alzheimer's Disease in a single living human individual.

In order to more fully understand and appreciate the present invention, the detailed disclosure below is divided into two sections. Section I describes the diagnosis of Alzheimer's Disease based upon neurotransmitter-stimulated changes in pupil diameter. Section II describes the diagnosis of Alzheimer's disease based upon light-stimulated pupil constriction velocity.

Section I: Diagnosis of Alzheimer's Disease Based Upon Neurotransmitter-Stimulated Changes in Pupil Diameter A. Modes for Performing the Diagnostic Method The present diagnostic methodology can be performed in any of at least three different modes; and within each of these alternative modes, at least two major variants are available regarding the class of neural transmitter mediator used and the manner in which changes in pupil diameter are observed and determined. Each of the three different alternative modes and the individual categories or classes of neural transmitter mediator are described in detail below.

1. Mode 1: Pupil Dilation (Mydriasis)

Apart from the methodology described in section II below, the most preferred mode of performing the diagnostic methodology utilizes the percentage change in pupil dilation as the diagnostic feature of choice. Pupil dilation is the response most easily observed and measured; and pupil dilation provides the greatest possible range of pupil diameter size changes and variances for the population as a whole.

In order to permit pupil dilation (rather than any other type of pupillary change) to occur at all as a demonstration of Alzheimer's dementia hypersensitivity, one must administer a dilute concentration of at least one neural transmitter mediator which is a recognized and conventionally known mydriatic agent. Typically this will be an agent selected from the group consisting of cholinergic antagonists, adrenergic agonists, or a combination of these agents. A representative, but non-exhaustive listing of these drugs provided in Table 2 below.

TABLE 2

Neural Transmitter Mediators

| Agent-Generic | Name Brand Example | Conventionally Used Doses | Present Use/ Comments |
|---|---|---|---|
| A. Anticholinergic Agents | | | |
| Tropicamide | Mydriacyl | 0.5–1.0% | Usually 1.0% |
| Atropine | Atropisol | 1% | Not routinely used for eye examinations in adults. |
| Homotropine Hydrobromide | I-Homatrine | 2% q 10–15 min | Used for refraction not dilation |
| Cyclopentolate Hydrochloride | Cyclogyl | 0.5–2% | 0.5% for fundoscopic examination |
| Scopolamine | Isopto Hyoscine | 0.2–0.25% | Used for post-op mydriasis not eye examinations |
| B. Adrenergic Agents | | | |
| Phenylephrine Hydrochloride | Mydfrin | 2.5% | — |
| Hydroxyamphe-amine Hydrobromide | Paredrine | 1% | — |
| Dipivefrin | Propine | 0.1 | For the treatment of glaucoma |
| Epinephrine | Epifrin | 1–2% up to 4x/day | — |
| C. Combined Agents | | | |
| Cyclopentolate Hydrochloride & Phenylephrine | Cyclomydril | 0.2% cyclopen & 1/% phenyleph. | — |

2. Mode 2: Pupil Contraction (Miosis)

An alternative mode for performing the diagnostic method utilizes pupil constriction as the diagnostic feature which is measured. Pupillary constriction is a second form of hypersensitive reaction demonstrated by an Alzheimer's disease patient as a consequence of the administration of another class of neural transmitter mediator—the miotic agent.

In order to allow pupillary constriction to occur as a manifestation of the hypersensitivity generated by Alzheimer's disease, one must administer a dilute concentration of at least one miotic agent to the eye of the subject under test. The pharmacologically active compounds are cholinergic agonists or adrenergic antagonists; and typically include the classes of parasympathometic agents, short-acting anticholinesterase agents and long-acting anticholinesterase agents. A representative, but non-exhaustive, listing is provided by Table 3 below.

TABLE 3

Miotics

| Agent-Generic | Name Brand Example | Conventionally Used Doses | Present Use/ Comments |
|---|---|---|---|
| A. Parasympathomimetic Agents | | | |
| Pilocarpine Hydochloride | Pilocar | 14% solution 1–6 times/day | For the treatment of glaucoma |
| Pilocarpine Nitrate | Pilagan Liquifilm | | |

TABLE 3-continued

Miotics

| Agent-Generic | Name Brand Example | Conventionally Used Doses | Present Use/ Comments |
|---|---|---|---|
| Carbachol | Isopto Carbachol | 0.75–3% solution 3–6 times/day | For the treatment of glaucoma |
| B. Short-Acting Anticholinesterase Agents | | | |
| Physostigmine Sulfate/ Physostigmine Salicylate | Eserine Sulfate Isopto Eserine | 0.25% solution 4+ times/day | For the treatment of glaucoma |
| C. Long-Acting Anticholinesterase Agents | | | |
| Demecarium Bromide | Humorsol | 0.125% = 0.25% q 12–48 hours | For the treatment of glaucoma |
| Echothiophate Iodide | Phospholine Iodide | 0.03%–0.6% q 12–48 hours | For the treatment of glaucoma |
| D. Beta-Adrenergic Antagonists | | | |
| Timolol Maleate | Timoptic | 0.25%–0.5% 2 times/day | For the treatment of glaucoma |

3. Mode 3: Rate of Pupil Diameter Size Changes

A third mode of performing the diagnostic method of the present invention utilizes the rate of change in pupil diameter size as the diagnostic feature. A markedly rapid velocity in pupil diameter change after administration of a neural transmitter mediator serves to identify the hypersensitive reaction of the person afflicted with Alzheimer's disease and distinguishes that person's pupillary response from those of cognitively intact persons. Clearly, the rate of change is the critical factor; and the pupil can be either dilated or constricted during the performance of the procedure in order to make the determination.

The mode of observation and measurement is the direct comparison of the rate of change for an individual being tested for Alzheimer's disease to those rates of change established in a population of age-matched and cognitively intact individuals. A substantive difference in rate of change from the population normal range of values would serve to diagnose Alzheimer's disease in the tested individual. A less desirable but alternative basis of evaluation would compare the rate of pupillary change for the treated eye against the rate of change for the untreated eye in the same individual.

C. Use Parameters and General Guidelines for Practicing the Diagnostic Method A range of general guidelines and use parameters are provided herein for the optimization and convenience of both the user and the individual being tested. These general guidelines are provided for the benefit of the intended user and are merely illustrative examples to consider when preparing detailed protocols intended for use on a clinical basis.

1. Duration of the Sampling Occasion.

An essential part of the present methodology is the use of a non-invasive automated apparatus to continuously monitor and repetitively measure pupil diameter size over time for a prechosen duration ranging from less than 1 second to about 5 minutes (300 seconds). Each continuous observation and repeated determination of pupil diameter size over time constitutes one "sampling occasion." As is described in greater detail hereinafter, the preferred automated apparatus is able to monitor and measure pupil diameter size repeatedly and continuously at a rate of at least 60 determinations per second. However, automated apparatuses which perform the requisite functions at a slower rate (e.g., less than 20 determinations per second) can also be used. It will be readily recognized that the quantum of data available for analysis will increase as the duration of measurement increases. Thus, for data obtained at a rate of 60 determinations per second, a one second duration yields 60 individual measurements of pupil diameter size whereas the preferred duration of about 30 seconds would yield 1800 individual measurements of pupil diameter size, with the entire 30 second interval constituting one sampling occasion. Thus, longer duration times produces more data for subsequent mathematical analysis.

The present invention requires that sufficient data be obtained to provide a statistically meaningful measure of pupil diameter. Low frequency measures or short durations of measurement provide insufficient data for statistical purposes and, ordinarily, will fail to provide a meaningful or reliable diagnosis. Accordingly, as noted above the present invention provides for repetitive measurements during each sample occasion or episode. Using a convenient sampling frequency of 60 Hertz allows for a reasonable permits statistically useful data to be obtained provided that sampling is continued for preferable at least 20 and more preferably at least 30 seconds.

The present methodology allows for a choice in the duration of time constituting one "sampling occasion." This duration of time should be kept reasonably constant and uniform during the entire diagnostic protocol and will constitute the standard number of seconds or minutes for each sampling occasion. In addition, the full chosen duration of time constituting the sampling occasion may be achieved in two, alternative, formats: as a single, uninterrupted interval time for continuous monitoring and repetitive measurement; or as a series of discrete time aliquots in sequence with slight pauses (typically seconds) interrupting the monitoring and measurement process.

With the illustrative preferred automated apparatus providing 60 determinations per second, a 30 second duration sampling occasion is deemed to be adequate and reliable for diagnostic determination purposes. Alternatively, if the apparatus at hand is a much slower operating instrument offering—for example, only 20 determinations per second—then a somewhat longer duration of time constituting each sampling occasion interval may be desirable. Similarly, with the advent and manufacture of ever more rapid automated instrumentation, measurement speeds far greater than 60 determinations per second are envisioned, and accurate determinations may be made at sampling occasions of shorter duration.

2. Frequency of Sampling Occasions

At least two sampling occasions, separated by a prechosen length of time, should be made when practicing the present diagnostic method. The first sampling occasion constitutes the "zero" time and provides the initial baseline characteristics of untreated pupil diameter size for that individual patient. It is expected and intended that this initial baseline sampling occasion be made on both the left eye and the right eye of the patient. In general, either of the two eyes may be used as the targeted eye for subsequent treatment with a neural transmitter mediator. The untreated control eye in turn will receive a drop of sterile water.

After performing the baseline measurement, the present diagnostic method requires that at least a second sampling occasion be performed, preferably when the maximum difference in pupil diameter change or pupillary response occurs. The methodology therefore requires at least two different sampling occasions of specified duration during which the treated targeted eye and desirably the non-treated controlled eye are monitored and measured. In preferred protocols, however, from 3 to about 6 different sampling occasions are performed over a period of about one hour. The greater number of sampling occasions within the overall protocol will allow a plotting and empirical determination which more accurately identifies the pupillary response peak or the maximal effect of treating the targeted eye with the chosen neural transmitter mediator. Thus, the preferred protocol will have 6 different sampling occasions of, for example, 30 seconds duration each (assuming the automated apparatus can provide a capability of 60 determinations per second).

3. Concentration of the Chosen Neural Transmitter Mediator

In the preferred mode of practicing the present diagnostic methodology, the concentration of neural transmitter mediator should be such that it will not markedly affect the pupillary responses of cognitively intact people, not afflicted with Alzheimer's dementia. For example, it has been empirically determined that the concentrations of tropicamide which are insufficient to cause such pupillary responses in normal individuals includes a range of concentration from 0.0025% to about 0.01%. Thus, the range of tropicamide concentrations may be used in the present method includes 0.0025%, 0.005%, and 0.01%.

Depending on the concentration of neural transmitter mediator actually used, the amount of time before pupillary responses show the most significant differences between Alzheimer's patients and normal controls may differ; and thus the time of maximal response may vary. For example, it is estimated that a concentration of 0.01% tropicamide will result in a maximum pupillary dilation response at about 29 minutes after its administration to the targeted eye in an Alzheimer's patient. Thus, the repetitive and episodic measurements of pupil diameter would continue up to and including this period of expected maximal response to facilitate determination of the most significant possible difference between a possible Alzheimer's patient and the established value for a normal control.

It will also be appreciated that in the less desirable modes, the test method can employ a use concentration or strength of neural transmitter mediator which is sufficient to cause some noticeable change in pupil diameter and pupillary response even in a normal, non-Alzheimer's individual.

4. Preferred Basis for Comparing the Empirically Obtained Result in Order to Diagnose Alzheimer's Disease A diagnosis is preferably made when the change (or rate of change) in pupil diameter of the eye treated with either a cholinergic or adrenergic antagonist or agonist exceeds a predetermined range of numerical values representative of the cognitively intact population as a whole. This range of numerical values is considered the diagnostic criterion for determining the presence or absence of Alzheimer's disease in a living human individual. The diagnostic evaluation is empirically determined by examining the percentage change in pupil diameter and fate of change) for diagnosed Alzheimer's patients and for known cognitively intact individuals for a particular neural transmitter substance at a particular concentration; and determining the point at which known Alzheimer's patients compared to known cognitively intact individuals are distinguishable.

D. Preferred Protocols

It will be appreciated that the preferred protocols presented herein are merely illustrative of the diagnostic methodology as a whole and are intended to be modified in a substantive manner to practice the different modes described previously herein as well as to accommodate different automated equipment and clinical circumstances.

The preferred protocols employ the pupil dilation mode of analysis; utilize dilute concentrations of a cholinergic antagonist as the pharmacologically active neural transmitter mediator; and use either a series 4000 TV based eye measurement system or PUPILSCREEN pupillometer as the automated apparatus for taking repeated diameter size measurements.

1. A First Preferred Protocol for Performing the Diagnostic Methodology a) Prior to beginning the pupil assay, the following patient screening tests must be done.
   1. Evaluate the patient for any ocular abnormalities:
      a. cataracts.
      b. history of glaucoma.
      c. a narrow anterior chamber.
   2. If patient exhibits condition "c" do not proceed with the test.
   3. If patient has cataracts that distort the shape of the pupil excessively do not administer the neural transmitter mediator to the affected eye.
   4. Screen patients for any current use of drugs with central or peripheral cholinergic effects. If patient is currently using medications with known cholinergic effects note on patient record for future reference in interpreting pupil assay data.

b) Once screening has been done, insure that the patient is alert and not agitated or drowsy. If patient is excessively drowsy do not proceed with test, but schedule the patient for future testing.

c) Allow three minutes for the patient to sit quietly while pupils adjust to ambient photopic illumination of no greater than 5 foot candles in the examining room.

d) After three minutes, image the patient's eye with a series 4000 TV based eye measurement system. Set the pupil discriminator so that the eye is completely encircled with the white discriminator and forms a clean elliptical image in the center of the pupil monitor. Open a data file and begin recording pupil diameter. Close the data file after measurements have been recorded for 1 minute. Open a second file and image the other eye as described above. Record 1 minute of baseline data. Each minute of observation will yield 3600 individual measurements of pupil diameter.

e) After completing the baseline readings and saving this data to disk, administer a single drop of the chosen neural transmitter mediator at the appropriate use concentration (e.g., a 0.01% tropicamide solution) to one targeted eye, chosen arbitrarily. The drop should be administered in the following manner:
   1. Have the patient in a position on a chair or an examining table so that they can tilt their head well back.
   2. Hold open the lower and upper eyelid with the thumb and first finger.
   3. Squeeze the bottle of treatment solution gently so as to allow a single drop to fall on the center of the lens of the eye.
   4. Have the patient close his/her eye after administration of the drop.
   5. Administer gentle pressure on the inner canthus of the eye for 1 minute to prevent excessive entry into the systemic circulation.

f) After 1 minute have the patient sit up. Wait one minute for the eye to adjust to ambient illumination and proceed to image the pupil as described in d) above. Record 30 seconds of pupil diameter to a data file. This duration of pupil diameter observation and measurement will yield approximately 1800 individual determinations of size.

g) Repeat the procedure in steps e) and f) with the other non-treated eye but using a single drop of sterile water for ophthalmic use in the place of neural transmitter mediator.

h) After administration of the sterile water drop to the non-treated eye and measurement of the non-treated pupil, have the patient wait quietly for a period of five minutes while viewing a video tape on the CRT monitor.

i) After 5 minutes have elapsed, turn off the video tape and wait for 1 minute while the patient's eye accommodates to the low illumination. Open a data file and image the eye as described in d). Record pupil diameter from the treated eye for 30 seconds. Repeat this procedure with the untreated eye. Each 30 second pupil diameter measurement occasion will yield approximately 1800 individual readings of pupil diameter size for each eye.

j) Repeat this procedure every 5 minutes until minute 30.

k) After the last reading at minute 30 have the patient view the video tape for 10 minutes. After 10 minutes record pupil diameter from the treated and untreated eyes as described above.

l) Have the patient view a final 10 minute segment of video tape and record pupil diameter from the treated and untreated eyes as described above. The final reading should be taken approximately 55 minutes after administration of the eye drops.

2. A Second Alternative Preferred Protocol for Performing the Diagnostic Methodology a) Screen patients as described above in step a) of the first preferred protocol.

b) Once screening has been done insure that the patient is alert and not agitated or drowsy. If patient is excessively drowsy do not proceed with test, but reschedule the patient for future testing.

c) Allow three minutes for patient to sit quietly while pupils adjust to ambient photopic illumination at no greater than 60 foot candles in the examining room.

d) After three minutes take five pupil measurements of 10 seconds duration each with the PUPILSCREEN assay instrument of each eye for baseline comparison. This will yield 1000 samples of pupil diameter data.

e) After completing the baseline readings and saving this data to disk, administer a single drop of the chosen neural transmitter mediator at an appropriate use concentration (e.g., a 0.005% tropicamide solution) to one targeted eye chosen arbitrarily. The drop should be administered as described above in step e) of the first preferred protocol.

f) After 1 minute have the patient sit up. Wait one minute for the eye to adjust to ambient illumination and proceed to take five pupil measurements of 6 seconds duration each of the treated eye. Wait approximately 30 seconds between each measurement cycle.

g) Repeat the procedure in steps e) and f) with the other non-treated eye but using a single drop of sterile water for ophthalmic use instead of neural transmitter mediator.

h) After administration of the sterile water to the non-treated eye and measurement of the non-treated eye, have the patient wait quietly for a period of five minutes. Repeat the measurements as specified in step f).

i) Repeat measurement cycle every 5 minutes up to minute 35 after administration of the tropicamide and sterile water drops.

E. Automated Instruments and Systems Suitable for Measuring Pupil Diameter Size A variety of non-invasive automated apparatus is known and commercially available which can be used or modified to meet the minimal operating requirements necessary when practicing the present diagnostic method. Three operational requirements are necessary:

(1) continuous monitoring of pupil diameter over time;

(2) repetitive measurement of pupil size diameter over a time ranging from less than 1 second to about 5 minutes in duration; and (3) Cumulative recording each measurement of pupil size diameter obtained over time.

A number of automated instruments can be used as is or modified to achieve performance of the minimal operating requirements. Examples of such conventional apparatuses are described in U.S. Pat. Nos. 4,755,043; 5,187,506; and 4,850,691. In addition, there is a varied class of instruments for measuring pupil diameter which are generally termed "pupillometers." A typical pupillometer measures, displays, and records pupil diameter before and after a light stimulus causes a constriction and redilation of the pupil. These instruments can be modified to eliminate the use of light stimuli to constrict and/or dilate the pupil artificially; and can also be modified to extend the typical manner of usage from making a single measurement to making repetitive measurements over a prechosen time duration in an uninterrupted manner. However, insofar as is known to date, none of these conventional systems has been employed for the diagnosis of Alzheimer's disease; and none of the software and hardware modifications have ever been employed clinically with such a diagnostic method.

The primary purpose and essential function of the automated systems is the multiple measurement of pupil diameter size in a serial and repetitive manner to yield a total of at least about sixty and often many thousands individual determinations. The apparatuses described herein—the Series 4000 TV eye movement measurement system and the PUPILSCREEN pupillometers and measurement systems—can determine pupil diameter size every $1/60$ or $1/20$ of a second; and serially repeat this measurement technique for a short or an extended time period over a desired number of seconds or minutes in duration. Thus, these instruments and systems provide 20–60 individual pupil diameter size determinations per second for as long as deemed necessary or desirable by the user. It is for these reasons that these non-invasive instruments and system are most preferred for use when practicing the present invention.

1. A First Non-Invasive Measuring Apparatus

A preferred non-invasive automated apparatus used for performing the diagnostic methodology which is the present invention is the commercially available Series 4000 eye movement measurement system (Applied Science Laboratories, Waltham, Mass.). This measurement apparatus and instrumentation was employed with cognitively intact individuals and with Alzheimer's disease patients in the experiments described hereinafter; and provides the empirical data presented subsequently which illustrate the operability, utility and value of the present diagnostic procedure as a whole.

The measurement system employed experimentally is an advanced eye tracker, unobtrusively measuring point of gaze and pupil diameter with sophisticated data recording and processing capabilities. A TV camera with a telephoto lens (pupil camera) is directed at one of the subject's eyes. A collimated, near infrared light source that is beamed coaxially with the pupil camera illuminates the eye. The light source is barely visible to the subject as a dim red light. A second TV camera (locating camera) provides a wide angle view of the head to simplify locating the eye. The pupil camera, locating camera, and light source are all enclosed in a single housing called the optical head which can be located up to 230 cm. (90 inches) from the eye. Sixty individual measurements are made each second; and a 30 second viewing duration of the pupil will yield 1800 individual data measurements for the single viewing occasion. The video data is preprocessed, digitized, and sent to an attached computer by the electronics unit as it comes from the camera 2. A Second Non-Invasive Measuring Apparatus Other desirable apparatuses for continuously monitoring pupil diameter size, for repetitively measuring pupil diameter, and cumulatively recording measurement data over time in an uninterrupted manner are the commercially available Pupillometer systems (Applied Science Laboratories, Bedford, Mass.). These instruments and systems, in a modified form for clinical use, are well suited for practicing the present methodology to detect Alzheimer's disease in living human subjects. The pupillometer apparatus provides accurate, real-time measurement and display of pupil diameter. The pupil is continuously monitored and pupil diameter is shown directly on a panel meter and also in digital and analog forms. Measurement is also independent of eye movement and other variations over a large field of view. Whereas the TV pupillometer offers accuracy, maximum system flexibility, and high sampling speed, the clinical and field system devices offer simplicity of use, portability, and automatic data recording and display. These devices are ideal for studies primarily concerned with pupillary reflex function and fast subject output.

F. Experiments and Empirical Data

To demonstrate the diversity and range of the diagnostic method comprising the present invention, several experimental studies and individual human case history reports are provided below. These experiments and human case history reports are illustrative embodiments of the present invention; and also effectively illustrate the mode and manner in which the diagnostic method can be practiced to advantage. It will be expressly understood that these experiments and details do not either restrict or limit the present invention in any manner.

1. Experimental Series 1: Hypersensitivity of Alzheimer's Disease Patients a) Subjects A total of 58 individuals were tested for their pupil response to a very dilute solution of tropicamide. These subjects were divided into 5 experimental groups, two patient groups and three groups of elderly controls. The Alzheimer's patient group consisted of 14 subjects who had been previously diagnosed with probable Alzheimer's disease based on standard clinical criteria. A pilot sample of non-Alzheimer's type dementias consisted of 4 patients with a diagnosis of Korsakoff's syndrome, multi infarct dementia and dementia with an extrapyramidal syndrome. Based on neuropsychological screening criteria defined prior to the initiation of the study, 40 elderly subjects were assigned to one of 3 groups. Normal elderly controls consisted of 32 subjects who performed at or above age norms on a battery of neuropsychological tests, that assessed intellectual capacity, attention, memory and language. Five subjects whose performance yielded abnormalities in memory and discrepancies between estimated pre-morbid IQ and current performance in cognitive tests were classified as "suspect"

Alzheimer's individuals. Three elderly subjects who exhibited abnormal findings on cognitive tests but had no salient memory deficit were classified as "cognitively abnormal" elderly for this study.

The fourteen patients with a diagnosis of probable Alzheimer's disease, males and females, mean age 74±7, were drawn from the Massachusetts Alzheimer's Disease Research Center, Boston. Patients with probable Alzheimer's disease met strict NINCDS-ADRDA diagnostic criteria (see below) for probable Alzheimer's disease, and performed significantly worse than the 32 cognitively normal elderly controls on the Information-Memory-Concentration subtest of the Blessed Dementia Rating Scale, a standard clinical measure of disease severity, (AD=17±7 range=4–27; NC=0.7±0.85 range=0–3; p<0.01). The scores on the Blessed Dementia Rating Scale range from 0 to 37 with 37 representing the most severe impairment.

The NINCDS-ADRDA criteria for a diagnosis of probable Alzheimer's disease require that (i) dementia be established by clinical examination and be documented by a measure such as the Blessed Dementia Rating Scale, (ii) the patient exhibits deficits in 2 or more areas of cognition, (iii) there is a progressive worsening of memory and other cognitive functions, (iv) the patient has no disturbance of consciousness, (v) there is an onset between the ages of 40 and 90, (vi) there is an absence of systemic or brain diseases that in and of themselves could account for progressive deficits in memory and cognition.

Forty-three elderly controls, either spouses of patients or healthy volunteers recruited through advertisement in the metropolitan Boston area were initially enrolled in this study. Three elderly subjects did not meet screening criteria because Of significant ocular pathology (see below) and were not studied. Of the 40 elderly subjects, mean age 72±6 (no significant difference from patients), who participated in the study, 32 were considered cognitively normal based on neuropsychological screening. A pilot sample of four patients with a diagnosis of non-Alzheimer's type dementia were also included for study, mean age 66±6. Two of these patients carried a primary diagnosis of Korsakofrs syndrome, one carried a diagnosis of multi-infarct dementia and one a dementia with an extrapyramidal syndrome.

All subjects completed an informed consent agreement. With the exception of the patient with the extrapyramidal syndrome (i.e., Parkinsonian-like) all subjects had unremarkable findings on a neuro-ophthalmological examination evaluating saccades, smooth pursuit, visual fields to confrontation and partial field optokinetic nystagmus. No subjects were accepted into the study with glaucoma, iridectomies or if they were found to have a narrow anterior chamber predisposing them to closed angle aucoma in response to tropicamide. Three potential normal controls volunteering for this study were not tested due to iridectomies in one or both eyes. No potential subjects were rejected on the basis of narrow anterior chamber. Normal controls had no diseases of the central nervous system by history. Medication use in patients and all control subjects was comparable. No subject was taking medications with known interaction effects with tropicamide. Patients were not taking any experimental acetylcholinesterase inhibitors (e.g. Cognex) that might interfere with the assay.

b) Preliminary Eye Measurements

All subjects were tested at the Laboratory of Eye Movements and Higher Cortical Functions at the Behavioral Neurology Unit at Beth Israel Hospital. Pupil diameter was measured using an Applied Science Laboratories video based, near infrared pupil center to corneal reflection system as described previously herein. This system measures pupil diameter sampled continuously at 60 hertz, is non-invasive, and requires no subject attachments or restraints. For this study, each subject was seated in a comfortable room with dim ambient illumination at a distance of 1.5 m in front of a TV screen.

The subjects' pupils were imaged and measured by the system as they sat viewing the TV screen set at a uniform low illumination. Subjects were directed to look at the center of the screen while each of the eyes was individually imaged. Once the eye was adequately imaged and subjects had ample time to adjust to ambient illumination, a short calibration procedure was performed to insure accurate monitoring of subjects' eye position. Pupil diameter data from the left eye and the right eye of each subject was sampled for 1 minute each to serve as baseline measures of pupil diameter.

c) Neural Transmitter Mediator

Pupil dilation (mydriasis) of Alzheimer's and control subjects was elicited by the topical application of a cholinergic antagonist, tropicamide, in one targeted eye. Tropicamide, a synthetic analog of atropine commonly used in ophthalmology to dilate the pupil and allow examination of the Fundus, takes advantage of the fact that some of the nerves that control the iris muscle use acetylcholine as a neurotransmitter. Typically, 0.5% to 1.0% solutions of tropicamide are used to dilate the pupil maximally in 20 to 40 minutes in normal, healthy subjects. The concentration of tropicamide (0.01%) used in this study was chosen so as to cause minimal or no dilation of a pupil in a cognitively intact individual, a non-Alzheimer's person.

The choice of using a 0.01% tropicamide concentration for diagnosis determinations was empirically based. Prior to diagnostic testing, experiments with various solution strengths (0.5%–0.01%) were performed to determine the strength concentration that would produce minimal or no dilation (mydriasis) in healthy controls in order to maximize the observed differences in comparison to the AD patient group. Although the entire concentration range experimentally evaluated (0.5%–0.01%) caused some pupil dilation, the higher concentrations caused a maximal dilation rather than a minimal effect. Thus, when tropicamide is employed as the neural transmitter antagonist, the 0.01% concentration is preferred.

d) Protocol and Eye Measurement Procedure

After baseline pupil diameter measures were obtained from both eyes, either the right or left eye (randomly chosen) was treated with a single drop of 0.01% tropicamide solution. Risks to patients and controls were minimized by applying pressure to the inner canthus of the treated eye for 1 min. to reduce systemic absorption of the drug.

Pupil diameter data was sampled from the treated eye and the untreated eye individually for 30 sec. durations repeatedly at fixed intervals over the course of an hour as the sampling schedule. Pupil diameter was observed, measured and data obtained at 0, 2, 8, 15, 22, 29, 41 and 53 minutes after administration of tropicamide to one eye; and 30 seconds response was observed and measured at each of these scheduled measurement points-thereby yielding 1800 individual pupil diameter measurements per 30 second sampling duration. This yielded a total of seven samples of 30 sec. duration each from the tropicamide treated eye and seven samples of 30 sec. duration each from the untreated eye during the course of the measuring protocol.

e) Results

The resulting data reveals and unequivocally demonstrates that AD patients have a defect in pupil response compared to normal subjects. This is shown by FIGS. 3–6 respectively which provide data from two the experimental groups.

Figure 3:
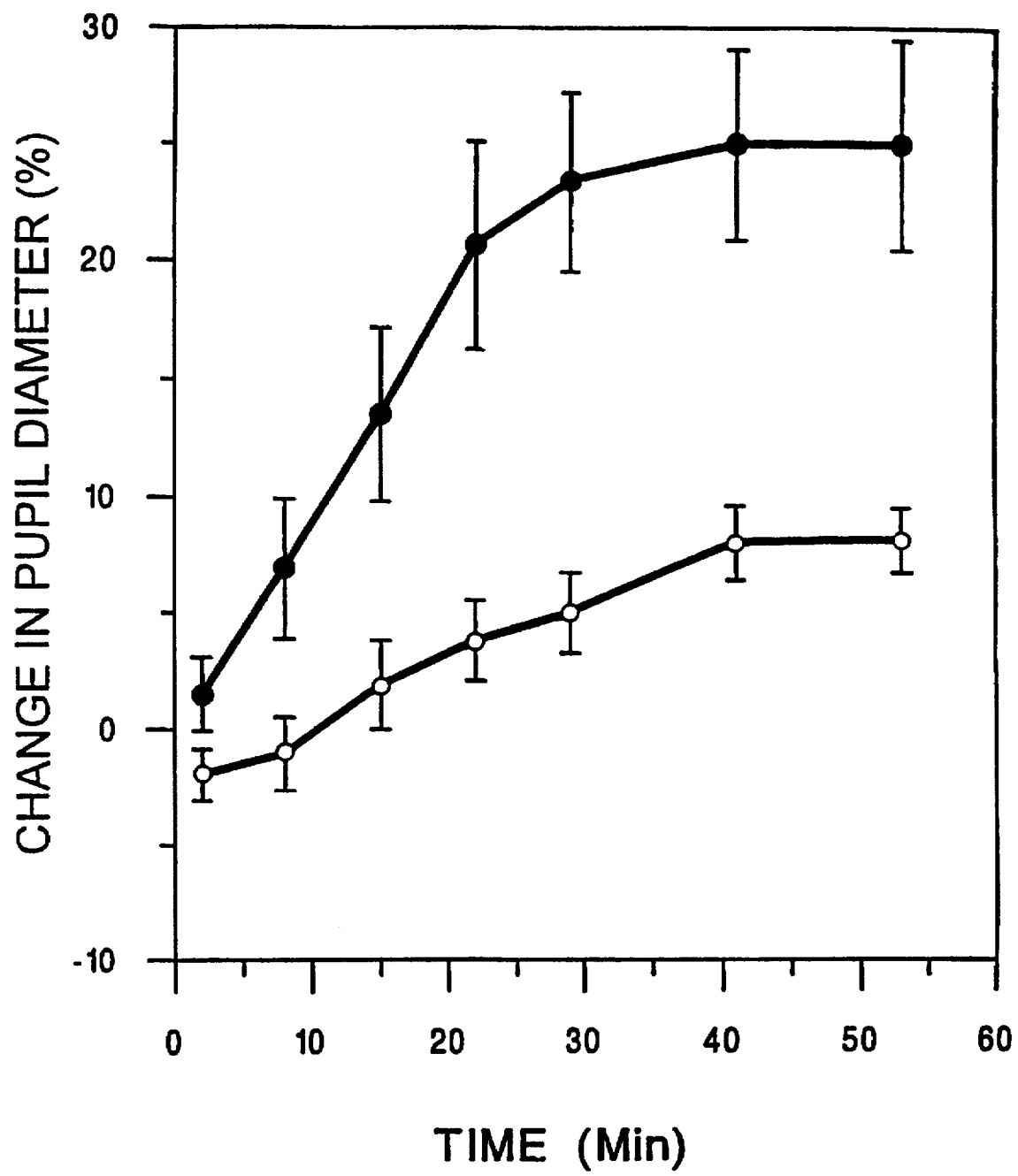
FIG. 3 is a graph illustrating the differences in pupil dilation responses to a cholinergic antagonist between patients with clinically determined Alzheimer's disease and cognitively intact elderly individuals obtained using the present methodology. Results for patients clinically diagnosed as having Alzheimer's disease are denoted by darkened circles and results for cognitively intact elderly individuals by open circles.

FIG. 3 compares the pupil dilation response of patients with clinically determined Alzheimer's disease and experimental controls. As illustrated by FIG. 3, the treated pupils of the normal elderly controls showed a minimal increase in pupil diameter over the course of the hour. In contrast the patients afflicted with Alzheimer's disease displayed a pronounced response to the pupil dilating effect of tropicamide as shown by the upper curve. Each time point shown in FIG. 3 represents the mean percentage change in pupil diameter over resting pupil diameter (baseline) measurement in the treated eye of Alzheimer's patients and normal elderly controls. A Kurskal Wallis pairwise multisample test was used to determine the significance of the differential tropicamide sensitivity of the Alzheimer's and control groups. Overall the results indicated that at minute 29 there is a 23.4% (SEM 3.8%) change in the pupil diameter of patients with probable Alzheimer's disease compared to a 5% (SEM 1.7%) change for normal elderly subjects (p=0.009).

Figure 4:
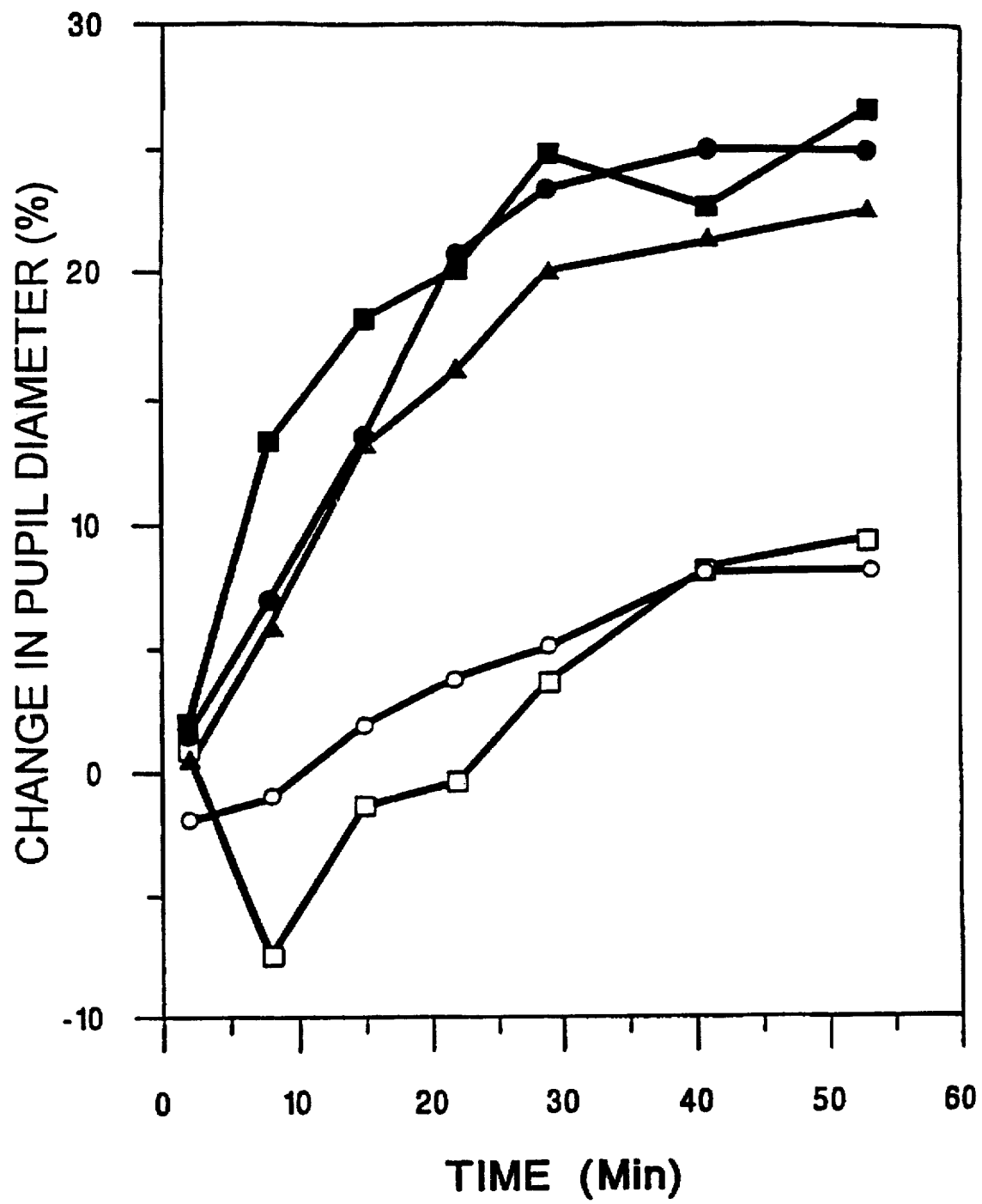
FIG. 4 is a graph illustrating the differences in pupil dilation response to a cholinergic antagonist among patients with clinically determined Alzheimer's disease, suspect Alzheimer's individuals, cognitively abnormal elderly subjects, patients with non-Alzheimer's dementia, and cognitively intact normal persons obtained using the present methodology. Symbols are as follows: darkened circles—results for patients clinically diagnosed as having Alzheimer's disease; darkened triangles—results for subjects suspected of having Alzheimer's disease; darkened squares—results for cognitively abnormal elderly persons; open circles—results for cognitively intact elderly persons; open squares—results for patients with non-Alzheimer's dementia.

FIG. 4 compares the response of patients with clinically determined Alzheimer's disease, the suspect Alzheimer's individuals, the cognitively abnormal elderly subjects, the patients with non-Alzheimer's type dementia, and the normal controls. As shown by FIG. 4, the percentage change in pupil diameter of the treated eye over baseline of the suspect Alzheimer's subjects and the cognitively abnormal elderly closely parallels that of the patients with probable Alzheimer's disease, while the patients with non-Alzheimer's type dementia exhibit a pattern like that of normal elderly controls. Both the suspect Alzheimer's disease individuals and the cognitively abnormal elderly subjects show an almost identical pattern of pupillary response to that of patients with clinically determined Alzheimer's disease. In contrast, the response of the group of patients diagnosed with non-Alzheimer's type dementia is similar to that of normal elderly controls.

Figure 5:
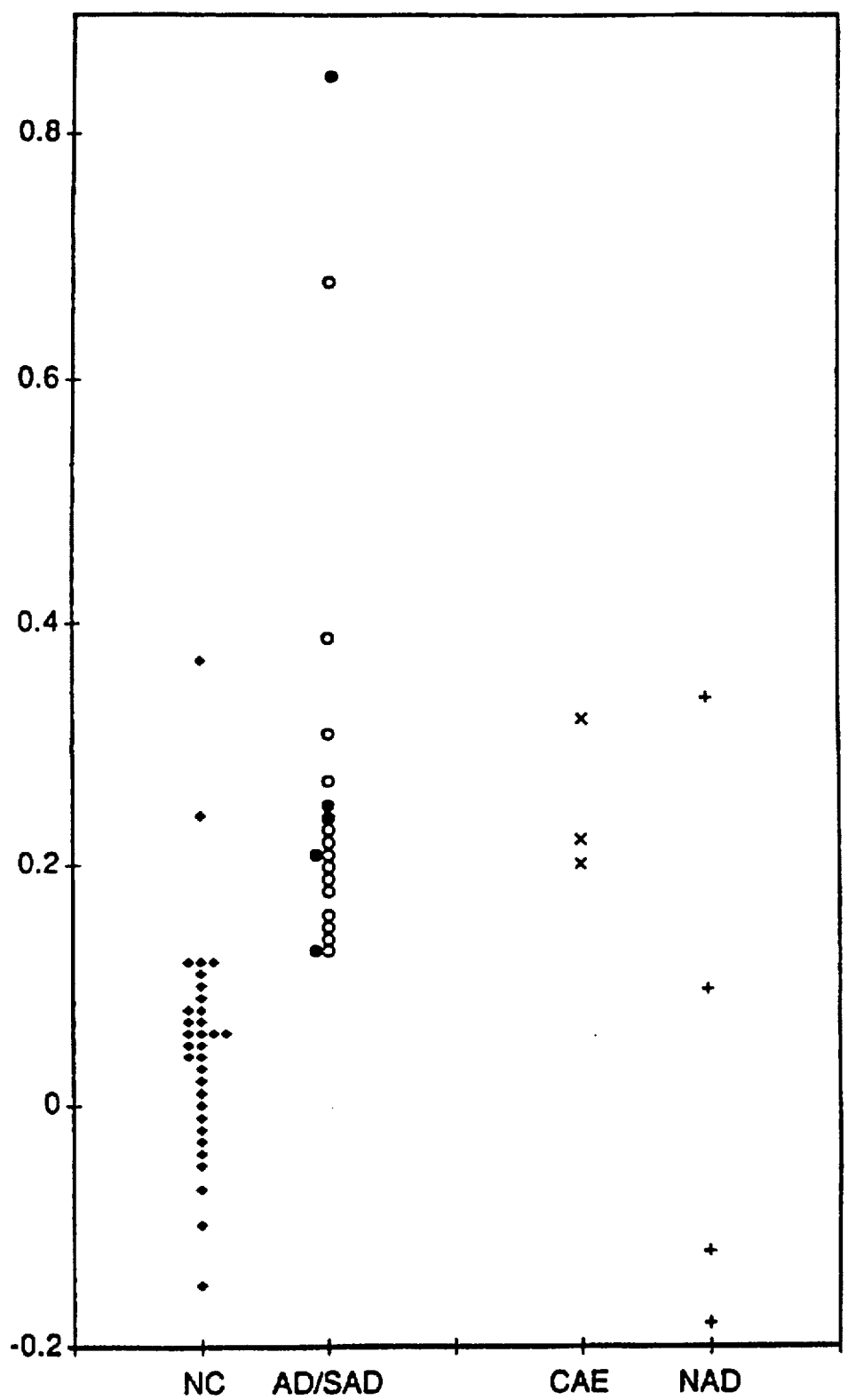
FIG. 5 is a scatter plot display illustrating pupil response data for the 29 minute sampling occasion for clinically determined Alzheimer's patients and cognitively intact elderly control subjects. Abbreviations are as follows: NC=normal control subjects; AD/SAD=Alzheimer's disease patients/suspect Alzheimer's disease individuals; CAE= cognitively abnormal elderly persons; NAD=non-Alzheimer type dementia patients.
Figure 6:
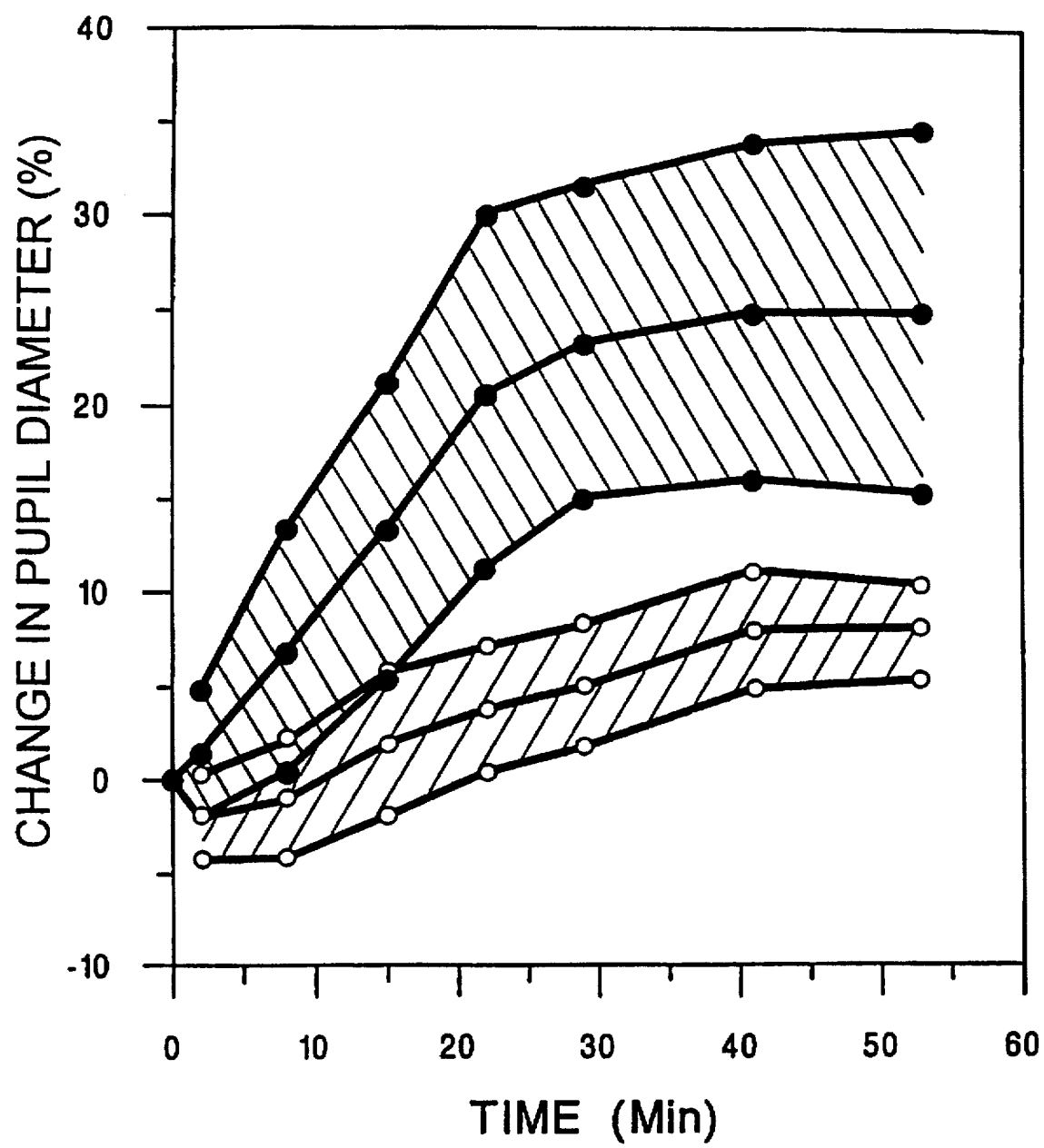
FIG. 6 is a graph illustrating the mean scores and +/−95% confidence limits of patients with probable Alzheimer's disease and cognitively intact elderly individuals obtained using the present methodology. Darkened circles represent results for patients with probable Alzheimer's disease and open circles represent represent results for cognitively intact elderly persons.

The complete set of data for the 29 minute sampling point (the point of maximal separation of clinically determined Alzheimer's patients and normal elderly control subjects) is presented by FIG. 5. Each symbol represents the percent change in pupil size over baseline of a single individual. FIG. 6 plots the mean scores and the ±95% confidence intervals of the means for patients with probable Alzheimer's disease and the normal elderly controls. There is a clear separation between these groups beginning at minute 15. This distinct separation between the groups is maintained at minute 29 after instillation for the ±99% confidence intervals (not shown).

Note that a minimum overlap in the pupil dilation scores between groups and between individual subjects in different groups is obtained by designating 13% change in pupil diameter at minute 29 of the assay as a cutoff point. Of the 40 elderly subjects from the community that were tested, (normal elderly controls (NC), suspect Alzheimer's dementia individuals (SAD), and cognitively abnormal elderly subjects (CAE)), 9 showed a positive response to the assay that was greater than or equal to 13% at minute 29, of which 7 were either in the suspect Alzheimer's disease group or the cognitively abnormal elderly group. Thus, only 2 of 32 normal elderly controls exhibited an exaggerated positive pupil response to the assay, but had no other clinically notable cognitive or neurological defects. This number of positive pupil responses in our "normal" elderly sample is within the order of magnitude one should expect from previous studies of the prevalence of this disease in the community. It is therefore believed that these 2 individuals may have sufficient Alzheimer's pathology to register a positive pupil finding, but do not yet exhibit clinically discernible symptoms of cognitive decline.

Of the 4 patients with non-Alzheimer's type dementia (NAD), included as a pilot sample, 3 showed a minimal response to the pupil assay and reacted as the normal elderly sample. One subject (diagnosed with Korsokoff's syndrome) exhibited a pupil response similar to that of patients with probable Alzheimer's disease.

These data indicate that, with few exceptions, both patients with a diagnosis of probable Alzheimer's disease and the subjects we have classified as "suspect" Alzheimer's individuals can be distinguished from the normal elderly controls on the basis of their hypersensitivity to tropicamide. Furthermore, the fact that the response of patients in the pilot sample with non-Alzheimer's type dementias is similar to that of normal elderly controls, shows that the pupil dilation assay is specific for Alzheimer's pathology.

When the data from the 14 patients is combined with probable Alzheimer's disease and the 5 subjects termed suspect Alzheimer's individuals, 18 of 19 exhibited a positive response to the pupil dilation assay. This 95% concordance between the clinical or suspected diagnosis and the results of the pupil assay is consistent with the finding in our dementia clinic that 95% of patients who are clinically diagnosed with probable Alzheimer's disease and who are subsequently brought to autopsy have pathologically confirmed Alzheimer's disease.

f) Conclusions

Several findings from this study demonstrate that the pupil dilation test is able to identify Alzheimer's patients prior to the onset of clinical symptoms of dementia. First, patients with a clinical diagnosis of Alzheimer's disease who exhibited an exaggerated mydriatic response included the most mildly demented individuals as measured by the Information-Concentration-Memory subtest of the Blessed Dementia Rating Scale and no correlation was found between patients' dementia scores and a positive pupil result. The lack of such a correlation suggests that the pupil assay may be sensitive to the earliest stages of the disease. Secondly, almost all elderly subjects living in the community who were tested and who showed a positive pupil response also exhibited neuropsychological deficits and most were found to have a salient memory impairment consistent with Alzheimer's disease.

Of particular interest is the case of patient SG (described in detail subsequently by Case Study 3). This elderly subject living in the community initially exhibited a positive pupil response to the test methodology but showed no obvious cognitive deficits and only a self report of mild difficulty with some daily living activities. He was re-tested nine months later and continued to show a positive pupil response. During this interval, patient SG exhibited a substantial decline (from 0 to 6) on the Information-Concentration-Memory subtest the Blessed Dementia Rating Scale and developed clear memory deficits. These results indicate that the pupil response assay was sensitive enough to detect an abnormal response in an elderly community-dwelling individual who subsequently developed symptoms consistent with a diagnosis of probable Alzheimer's disease.

In sum, patients with clinically determined Alzheimer's disease can be distinguished from normal elderly subjects and patients with non-Alzheimer's type dementia on the basis of pupil diameter changes induced by a dilute solution of a cholinergic antagonist applied to the eye. All but one of the patients with probable Alzheimer's disease showed a pronounced hypersensitivity to a neural transmitter mediator, tropicamide; and there were only 2 of 32 subjects in the normal elderly sample who exhibited a response similar to that of the Alzheimer's patients. Overall the findings from this experiment series show that with respect to normal elderly controls and patients with probable or clinically suspect Alzheimer's disease the pupil dilation assay has a sensitivity of 95% and a specificity of 94%. Unlike other biochemical and physiological tests now being developed, the pupil response test is safe, relatively non-invasive, sensitive, and easy to quantitate with already-available automated instrumentation.

2. Experimental Series 2: Human Case Studies a) Case 1: Patient With Probable Alzheimer's Disease AA is a 77 year-old woman, retired educator with a 5 year history of an insidiously progressive decline in mental state functioning which has left her increasingly dependent on her daughter to supervise her daily living activities. Her initial symptoms involved forgetfulness and this has subsequently gotten increasingly worse. Currently, she cannot recall events that have occurred 5 minutes before. Neuropsychological testing revealed a prominent amnesic syndrome. She had preserved attention, but had marked difficulties storing or retrieving new information and exhibited a rapid rate of forgetting. She also had a mild anomic aphasia. She scored a 14/37 on the Information-Memory-Concentration (IMC) Subtest of the Blessed Dementia Scale (BDS), which is in the mild-moderate range of severity. (A score of 37 is the worst a patient can do.) Her score on the left side of the BDS that evaluates daily living activities, habits, personality, and behavior was 8/28, consistent with mildly compromised functioning. (A score of 28 would represent the most impaired status.) Elementary neurological examination was within normal limits. Cranial magnetic resonance imaging (MRI) was unremarkable for her age. EEG showed non-specific slowing. Metabolic studies were within normal limits.

Her history, neurological examination, and pattern of neuropsychological deficits as well as her unremarkable work-up yielded the diagnosis of probable Alzheimer's disease and was consistent with NINCDS-ADRDA criteria. She exhibited a hypersensitive mydriatic response to testing via the preferred protocol with tropicamide.

b) Case 2: Patient With Probable Alzheimer's Disease

BB is a 66 year-old retired housekeeper with an eighth grade education who exhibited 2½ years of progressive cognitive decline. Initially there were occasional episodes of forgetting events or activities as well as noticeable word finding pauses. Currently, she has major difficulties remembering daily events, conversations and things that she may have read or seen on television. BB is requiring increasing supervision to manage her daily living activities. Neuropsychological testing revealed mild attentional difficulties with substantial problems storing and retrieving information after brief delay and a marked anomia. BB scored a 11/37 on the IMC Subtest of the BDS. Elementary neurological examination was unremarkable. MRI was within normal limits for age. BB's clinical history, pattern of neuropsychological impairments, and negative work-up led to the diagnosis of probable Alzheimer's disease. BB exhibited a hypersensitive mydriatic response to testing via the preferred protocol.

c) Case 3: Elderly Subject With "Suspect" Alzheimer's Disease

SG is a 79 year-old retired male executive, with a BA from Harvard College, who volunteered to participate in our study. During his initial test session he shared concerns about possible changes in his cognitive abilities. Clinically, it was suspected that he may be exhibiting very subtle problems with his cognitive and functional status. He scored a 6/28 on the left side of the BDS, suggestive of mild changes in his daily living activities. However, his score on the IMC Subtest of the BDS was 0/37, which clearly was within normal limits. On the preferred protocol tropicamide test, his pupil exhibited a hypersensitive response. He agreed to a follow-up evaluation.

Nine months later the subject was retested. He continued to show mild changes in his activities and interests (scoring an 8/28 on the left side of the BDS). His performance on the IMC Subtest of the BDS was now 6/37, consistent with mild cognitive impairment. Further neuropsychological testing revealed an estimated premorbid 10 in the 93 percentile (FSIQ of approximately 123). However, his performance on the Boston Naming Test was only low average and he exhibited clear memory problems, performing much below his estimated premorbid capacities. There was a marked loss of newly learned information after a delay period. Elementary neurological examination was unremarkable. These results suggested an early dementing illness, with a salient amnestic component. This neuropsychological pattern was consistent with the diagnosis of probable Alzheimer's disease.

d) Case 4: Elderly Subject with Suspect Alzheimer's Disease

HH is a right handed 78 year-old retired engineering executive with 17 years of education living with his wife in the community, who volunteered as a subject in a study of aging and Alzheimer's disease. The subject had an unremarkable medical history with no report of diabetes, hypertension, seizure or stroke. His background is remarkable for a father who had clinically diagnosed Alzheimer's disease in his early eighties. HH had an unremarkable neurological examination. His estimated pre-morbid IQ was 125. His performance on the Information-Memory-Concentration subtest of the Blessed Dementia Rating Scale was 0/37 with 0–3/37 being considered normal. Naming was unremarkable for age. However testing of attention revealed some mild impersistence. Memory performance appeared to be mildly impaired as tested on immediate and delayed recall on the verbal and visual portions of the Wechsler Memory Scale. HH encoded information adequately but lost information on delayed recall. On delayed visual recall he scored only at the 29th percentlie for age which is inconsistent with his estimated premorbid IQ. HH was sent for a SPECT scan which revealed perfusions defects in inferior temporal and superior parietal corticies consistent with the SPECT pattern seen in Alzheimer's patients.

The pattern of findings with this subject is consistent with mild changes in memory and attention. On the preferred pupil protocol, HH exhibited a positive response. He was classified as a suspect Alzheimer's patient.

e) Case 5: Patient with Dementia of the Non-Alzheimer's Type

BB is a 79 year-old priest with a Ph.D. in religious studies, who presented with an atypical Parkinsonian syndrome not responsive to Sinemet. His motor disabilities were characterized by bradykinesia, a "masked" face, hypophonia, micrographia, and slowed gait. These symptoms have been slowly progressive and are consistent with a degenerative disease affecting the basal ganglia and its connections. Over the past 4 years, he has exhibited progressive and marked decline in mental abilities. Initially, he scored a 2 on the IMC Subtest of the BDS. Four years later, he scored a 7. He has exhibited increasingly slowed cognitive processing speed, impaired complex attention, and memory difficulties due to limited attention span. Primary memory abilities (i.e. retention) and basic reasoning skills have been relatively well preserved (e.g. performing at the 98th percentile on the Ravens Progressive Matrices Test). His cranial MRI was unremarkable.

The patient's history and pattern of cognitive decline is not consistent with probable Alzheimer's disease. Rather, it suggests a dementing illness primarily affecting the frontal networks and their subcortical connections, sometimes referred to in the literature as a "subcortical dementia". BB's pupil dilation response to testing using the preferred protocol was within the normal range.

f) Case 6: Normal Elderly Control Subject

CC is an 87 year-old women who is living independently in the community and managing all of her daily activities and financial matters. She retired 20 years ago at age 67 and has remained socially active in her community. Past medical history was very benign, with no report of hypertension, diabetes, or strokes. She only scored 0.5/28 on the left-side of the BDS illustrating no significant alterations in activities, behavior, or personality. On the IMC Subtest of the BDS, she scored a 2/37 which is within normal limits. Her estimated 1Q was 121. Concentration and naming were unremarkable for her age. Immediate and delayed recall on the verbal and visual portions of the Wechsler Memory Scale were performed at the 80–86th percentile for elderly individuals. Her elementary neurological examination was benign. In summary, based on her current neurological, neuropsychological, and functional status, there is no evidence that she is suffering from a dementing illness and she fits all criteria for being a "normal" elderly control subject. Upon testing via the preferred protocol with the pupil response assay, she did not exhibit a hypersensitive response.

Section II: Diagnosis of Alzheimer's Disease Based Upon Light-Stimulated Pupil Constriction Velocity A. The Hypersensitive Pupillary Dynamic Responses If and when a person is suspected of having Alheimer'disease is clinically examined, the pupils of the subjects clinically examined, the pupils of the subject typically appear to be similar to those who are cognitively normal. The pupils of the Alzheimer's patient may be examined for size, shape, near response, and consensual light reaction without demonstrating any major defect. Light directed into one pupil will typically result in normal constriction of the pupils in both eyes. As with any population of individuals, some person's pupils may be markedly constricted; others may have unequal pupils; and the visual acuity of the person may be normal, show distant vision, or be near sighted. No casually observed feature of the pupil alone therefore can provide a basis for making a differential diagnosis.

In contrast, the hypersensitive dynamic responses of the pupil in the Alzheimer's disease patient present an observable, reproducible and reliable basis for clinical diagnosis. The pupils of Alzheimer's afflicted subjects respond abnormally to unusually small or dilute concentrations of exogenous neural transmitter mediators (cholinergic antagonists and agonists) intentionally introduced to the eye. Equally important, the pupil of the Alzheimer's patient responds to concentrations of neural transmitter modulators which cause little or no response in cognitively normal persons.

A range and variety of hypersensitive pupillary responses are individually identifiable and measurable in the Alzheimer's disease patient. For example, as described above in section I, the pupillary hypersensitive reaction can manifest itself as an abnormal mydriatic response to an unusually small concentration of an anticholinergic agent (such as 0.01% tropicamide); or as a miotic response to an unusually dilute concentration of a cholinergic agonist (such as 0.01% pilocarpine). In these examples, the hypersensitive pupillary response can be repeatedly observed and quantitatively measured (without any photostimulation) by determining pupil dilation or pupil contraction.

The method described in the present section employs an entirely different manifestation of the hypersensitive pupillary response. The hypersensitive manifestation observed, quantitatively measured, and utilized as the test parameter is the change in constriction velocity for the pupil in response to stimulation by visible light as a consequence of introducing a dilute cholinergic antagonist to the eye. The concentration of exogenous neural transmitter mediator (the cholinergic antagonist) administered to the eye of the subject is chosen so as to be insufficient to cause any marked pharmacological or physiological change in a cognitively intact normal person but is adequate to induce a substantive change in the pupil constriction velocity of the hypersensitive Alzheimer's disease patient. The manifestation thus identifying and distinguishing the Alzheimer's subject is the significant change in the constriction velocity of pupil response to photostimulation in comparison to cognitively normal persons receiving the same concentration of neural transmitter mediator.

B. The Essential Parts of The Methodology

There are four essential requirements for practicing the present diagnostic method, each of which may be satisfied with a variety of articles or procedures:

(1) The method requires the use of non-invasive means for introducing photostimulating visible light of predetermined wavelength and intensity to the eye sufficient to cause a constriction of the pupil; and for determining the velocity of the pupil constriction initiated by the photostimulation. A variety of preferred automated apparatuses and systems are described herein but the methodology as a whole is not dependent upon any specific apparatus, instrumentation, electronics, circuitry, optics, or system. Accordingly, any means which individually or integrally provides the requisite eye photostimulation and constriction velocity determination will suffice for purposes of practicing the present invention.

(2) The method requires the administration of at least one neural transmitter mediator to an eye of the person undergoing diagnostic testing. This mediator is a compound selected from the group consisting of cholinergic antagonists. Moreover, the quantity and concentration of this neural transmitter mediator must be sufficiently dilute such that a cognitively normal person receiving this mediator will not show or reveal a marked or substantive change in his constriction velocity after photostimulation.

(3) The method requires that at least one eye of the person undergoing diagnostic testing be subjected to stimulating visible light energy after administration of the neural transmitter mediator to that eye. The range of visible light wavelengths, visible light intensities, time duration of visible light stimulation, and frequency of repeated visible light stimulation may be varied. Accordingly, the substantive requirement is only that the eye of the test subject be stimulated by visible light after the introduction of a neural transmitter mediator.

(4) The method requires that the constriction velocity after photostimulation be determined after the neural transmitter mediator has been administered to the eye. This constriction velocity determination can be made using any article, machine, measurement system, method of calculation, and display mode conventionally known or commercially available.

C. The Diagnostic Method

1. The Neural Transmitter Mediator:

The present diagnostic methodology utilizes the constriction velocity of the pupil in response to stimulation by light as the essential diagnostic feature. In order to utilize pupil constriction velocity as a parameter (rather than any other type of pupillary dynamic change) one must administer a dilute concentration of a cholinergic antagonist. A representative, but non-exhaustive listing is provided by Table 4 below.

TABLE 4

| Exogenous Neural Transmitter Mediators | | | |
|---|---|---|---|
| Agent-Generic | Name Brand Example | Conventionally Used Doses | Present Use/ Comments |
| Anticholinergic Agents (cholinergic antagonists) | | | |
| Tropicamide | Mydriacyl | 0.5–1.0% | Usually 1.0% |
| Atropine | Atropisol | 1% | Not routinely used for eye examinations in adults |
| Homotropine Hydrobromide | I-Homatrine | 2% q 10–15 min | Used for refraction not dilation |
| Cyclopentolate Hydrochloride | Cyclogyl | 0.5–2% | 0.5% for fundoscopic examination |
| Scopolamine | Isopto Hyoscine | 0.2–0.25% | Used for post-op mydriasis not eye examinations |

It will be recognized and generally understood by a person ordinarily skilled in the anatomy of the eye that the pupil is formed by the muscles and pigmented stroma of the anterior uveal tract (the iris). There are two types of muscles: a circumferential sphincter found in the margin of the iris, innervated by the parasympathetic nervous system and radial dilator muscles which run from the iris margin to the root of the iris, innervated by the sympathetic nervous system. Pupil size represents a balance between stimulation from the parasympathetic and sympathetic nervous systems. Constriction of the pupil (miosis) is caused by the stimulation of the parasympathetic fibers, whereas dilation (mydriasis) is caused by sympathetic activation. These systems generally contain neurons that are driven by cholinergic or adrenergic neurotransmitters respectively. The neuro-physiology of the pupil and iris make it an ideal physiological marker for measuring the integrity of cranial nerve, midbrain and central nervous system functions.

2. Measurement Parameters and Procedural General Guidelines

A range of general procedural guidelines and measurement parameters are provided herein for the optimization and convenience of both the user and the individual being tested. These general procedural guidelines are provided for the benefit and advantage of the intended user; and the measurement parameters are merely illustrative possibilities, examples and suggestions to consider and use when preparing detailed protocols intended for use on a clinical basis.

3. The Repetitive Cycle and the Sampling Occasion

An essential part of the present methodology is the use of a non-invasive automated apparatus to monitor pupillary dynamic changes and to determine constriction velocity (the rate of pupil size changes) after stimulation by a known quantity of visible light energy. Each observation and individual determination of constriction velocity for the pupil constitutes one measurement "episode" or "epoch"; and a measurement episode is normally performed in less than seconds, e.g., the normal period of pupil constriction in response to photostimulation, and, further, is performed repetitively and cyclically. The preferred automated apparatus is able to monitor and measure pupil diameter size change repeatedly-both before and after photostimulation continuously at a rate of about 60 pupil measurements per second.

4. Frequency of Sampling Occasions

It is desirable that at least two sampling occasions separated by a prechosen length of time be made when practicing the present diagnostic method. The first sampling occasion constitutes the "zero" time and provides the initial baseline characteristics of untreated pupil constriction velocity for that individual patient. It is expected and intended that this initial baseline sampling occasion be made on both the left eye and the right eye of the patient. One eye, randomly chosen, will be the eye treated with the neurotransmitter mediator; and the other eye will be treated with a non-drug control solution.

The present diagnostic method and protocol demands that at least a second sampling occasion be performed after administration of the neural transmitter mediator to the targeted eye, preferably when the maximum change and difference in pupillary dynamic response occurs. The methodology preferably employs minimally two different sampling occasions during which the constriction velocity of the treated targeted eye and also of the non-treated control eye are measured. In better protocols, from 3 to about 6 different sampling occasions are performed after introduction of the neural transmitter mediator over a period of about one hour. This greater sampling will lead to results which more accurately identify the hypersensitivity of the pupillary response and the greatest change and maximal effects of treating the targeted eye with the chosen neural transmitter mediator. Thus, the preferred protocol will have 6 different sampling occasions of at least 5 measurement episodes each.

5. Concentration of the Chosen Neural Transmitter Mediator

Preferred embodiments will employ concentrations of neural transmitter mediator which does not cause significant changes in pupil constriction velocity vs. baseline prior to pharmacological treatment (meaningful changes in the rate of change for pupil diameter size) after photostimulation in individuals without Alzheimer's disease. In addition, the concentration should be high enough so that Alzheimer's disease patients show a marked hypersensitivity in pupillary response to photostimulation. Accordingly, neural transmitters and concentrations are, in general, determined and employed in the same manner as set forth in Section I.

6. Constriction Velocity Determination Cycles

The calculation of pupil constriction velocity is made using pupil diameter size data obtained both before and after photostimulation. Each cycle of repetitious measurement includes a first pupil diameter size determination, followed by photostimulation, and then a measurement of the stimulated (constricting) pupil. The pupil is then allowed sufficient time to re-dilate to its original diameter size state; and another measurement cycle to determine constriction velocity is then initiated. The preferred automated instruments described hereinafter can perform 5-60 pupil size measurements per second.

The initial and follow-up measurements of pupil size in each measurement episode are preferably made using near infrared light; and employ both the apparatuses and procedures described within U.S. Pat. Nos. 4,755,043 and 5,187,506, the texts of which are expressed incorporated by reference herein. Sources providing wavelengths of about 800 nm–2000 nm are used; and wavelengths from about 850 nm to 900 nm are deemed best. The light intensity is adjustable and preferably lies in the range of 1.5–6.5 mw/cm².

7. Basis for Comparing the Empirically Obtained Data in Order to Diagnose Alzheimer's Disease A diagnosis is preferably made when the pupil constriction velocity of the eye treated with either a cholinergic antagonist or agonist changes substantially and is significantly different than a predetermined range of numerical values representative of the cognitively intact population as a whole. The difference from the normal standard range of numerical values is considered the diagnostic criterion for determining the presence or absence of Alzheimer's disease in a living human individual. This diagnostic evaluation is empirically determined by examining the percentage change in pupil constriction velocity of known Alzheimer's patients and of known cognitively intact individuals to a particular neural transmitter substance at a particular concentration; and determining the point at which known Alzheimer's patients compared to known cognitively intact individuals are separable and distinguishable in the magnitude of their response.

D. Preferred Protocol

The present diagnostic method employs non-invasive automated apparatuses and systems which can observe and repetitively determine pupil constriction velocity over short time intervals in an uninterrupted manner. The manner of observation and repetitious measurement yields constriction velocity determinations of from about 5–60 measurements per sampling occasion. Different automated systems may vary in their speed of measuring pupil size changes, and the time duration of each sampling occasion may be extended or shortened accordingly.

The preferred protocol presented below is illustrative of the diagnostic methodology as a whole. The preferred protocol is intended to accommodate the different automated equipment and clinical circumstances in which persons suspected of being afflicted with Alzheimer's disease are to be encountered. The preferred protocol is as follows:

a) Prior to administering the pupil assay, the following patient screening tests must be done:
  1. Evaluate the patient for any ocular abnormalities:
     a. cataracts.
     b. history of glaucoma.
     c. a narrow anterior chamber.
     d. local corneal pathology that might affect corneal permeability (e.g., dry eye or poor tear lakes).
  2. If patient exhibits condition "b, c, or d" do not proceed with the test.
  3. If patient has cataracts that distort the shape of the pupil excessively do not administer the neural transmitter mediator to the affected eye.
  4. Screen patients for any current use of drugs with central or peripheral cholinergic effects. If patient is currently using medications with known cholinergic effects, note on the patient record for future reference in interpreting pupil assay data.

b) Once screening has been done, insure that the patient is alert and not agitated or drowsy, If patient is excessively drowsy do not proceed with test, but schedule the patient for future testing.

c) Allow five minutes for patient to sit quietly while pupils adjust to ambient photopic illumination at no greater than 5 foot candles in the examining room.

d) After five minutes, image the patient's eye with a 1050 Pupillometer eye measurement system. Set the pupil discriminator such that the eye is completely encircled with the white discriminator and forms a clean elliptical image in the center of the pupil monitor. Open a data file and begin recording pupil diameter data. Stimulate the eye by means of the photostimulator and continue to record data. Repeat this process after five seconds rest each time for an additional five measurement episodes. Repeat the entire procedure for the untreated eye.

e) After completing the baseline readings and saving this data to a file, administer a single drop of the chosen neural transmitter mediator in the appropriate concentration (e.g., a 0.01% tropicamide solution) to one targeted eye chosen arbitrarily. The drop should be administered in the following manner:
  1. Have the patient in a position on a chair or an examining table so that they can tilt their head well back.
  2. Hold open the lower and upper eyelid with the thumb and first finger.
  3. Squeeze the bottle of treatment solution gently so as to allow a single drop to fall on the center of the lens of the eye.
  4. Have the patient close his/her eye after administration of the drop.
  5. Administer gentle pressure on the inner canthus of the eye for 1 minute to prevent excessive entry into the systemic circulation.

f) After 1 minute have the patient sit up. Wait one minute for the eye to adjust to ambient illumination and proceed to image the pupil as described in (d) above. Record 5 seconds of pupil constriction velocity determinations separated by 30 second intervals to a data file.

g) Repeat the procedure in steps (e) and (f) with the other non-treated eye but using a single drop of sterile water for ophthalmic use.

h) After administration of the sterile water drop to the non-treated eye and measurement of the non-treated pupil have the patient wait quietly for a period of 5 minutes.

i) After 5 minutes have elapsed, wait for 1 minute while the patient's eye accommodates to the low illumination. Proceed to image the eye again as described in step (f). Record five constriction velocity measures from the treated eye. Repeat this procedure with the untreated eye.

j) Repeat the pupil constriction velocity determination procedure every 5 minutes until about minute 30 of the test.

k) After the last reading at about test minute 30, have the patient wait for 10 minutes more. After 10 minutes, again record pupil constriction velocity determinations from the treated and untreated eyes as described above.

l) Have the patient wait a final 10 minute segment and then record pupil constriction velocity determinations from the treated and untreated eyes as described above. The final reading should be taken approximately 55 minutes after administration of the eye drops.

E. Automated Instruments and Systems Suitable for Measuring Pupil Constriction Velocity.

A variety of non-invasive automated apparatuses are known and commercially available which can be used as is or modified quickly to meet the minimal operating requirements necessary for practicing the present diagnostic method. Examples of such conventional apparatuses are described in U.S. Pat. Nos. 4,755,043, 5,187,506; and 4,850,691. In addition, the "pupillometers" described above in section I may be used. The apparatuses described below can determine pupil constriction velocity every 1–3 seconds; and repeat this cyclically for a short or an extended time period.

1. First Non-Invasive Apparatus: A Photostimulator/Controller in Combination with a TV Pupillometer The Series 1000 Photostimulator and Controller is a powerful device for tests involving the introduction light pulses to one or both eyes of a subject. The beams of light are controllable in exposure frequency, pulse width, focus, beam diameter and intensity. For pupillometry, the Photostimulator/Controller may be used with the companion Applied Science Laboratories Series 1050 TV Pupillometer. One or both eyes may be light stimulated; and the controls for the two eye channels may be synchronized in any desired phase and temporal relationship in order to test binocular responses.

The controller provides a very convenient way of programming the shutter exposure times for one or two channels. The pulse width and the period may be controlled for each channel, and the phase relationship between the two systems can also be determined. This provides virtually any pulse profile that may be desired. Continuous cyclic operation or single pulse actuation is possible. The two channels may be locked phase or randomly related.

The Model 1050 TV pupillometer provides accurate, real-time measurement and display of pupil diameter. The pupil is continuously monitored; pupil diameter is shown directly on a panel meter; and pupil diameter is shown in digital and analog forms. Pupil diameter measurement is independent of eye movement and other variations over a large field of view.

The TV pupillometer uses a near infrared illuminator and a low light level, solid state CCD television camera to observe the eye. A pupil recognition circuit automatically distinguishes the pupil from the iris, the eyelids, and other noise with minimum operator adjustment. A television monitor displays the image of the eye with superimposed pupil delimiters to clearly indicate the accuracy of the measurement. The automatic circuitry will maintain proper measurement for a large range of settings and conditions.

In operation, the subject's head is usually stabilized by a chin rest or a chair with a headrest. There must be an unobstructed visual path to the eye. The operator then adjusts the optics and monitor to obtain a clear image of the subject's eye. Afterwards, the operator adjusts the discriminator control until a crescent appears at the left edge of the pupil and delimiters appear in the monitor above and below the pupil. As long as the delimiters are properly positioned, the measurement of pupil diameter is correct, in spite of any other noise or artifacts. Pupil diameter in millimeters is displayed on a panel meter and provided as analog and digital signals. Pupil diameter size is usually measured vertically; however, horizontal diameter and pupil area measurement are also possible.

2. Second Non-Invasive Apparatus: The PUPILSCAN System

Whereas Model 1050 offers accuracy, maximum system flexibility, and high sampling speed, the S-6 and S-7 devices offer simplicity of use, portability, and automatic data recording and display. The S-6 and S-7 devices are ideal for clinical or field studies primarily concerned with pupillary reflex function and fast subject throughput. The S-6 device, also known as the PUPILSCAN™ apparatus, is a binocular tabletop device. Both devices are interfaced to any IBM compatible PC via a conventionally supplied interface board and cable.

When the trigger position operating switch an the S-6 optical unit is depressed, infra-red illumination is turned on and a reflected image of the pupil is focused on an electronic image sensor. The illumination is adjusted automatically by the program to the optimum level simplifying use under widely variable ambient light conditions. To aid in centering the instrument on the pupil, a pair of red diodes on the cross hair ring are illuminated or extinguished when satisfactory image position has been achieved as a signal to the operator to release the operating switch to make the measurement. When the switch is released, the program fine tunes infrared illumination and automatically fires selectable intensity green diodes for a programmed duration stimulus pulse.

Maximum velocity of constriction is displayed in millimeter per second and the amplitude of pupil constriction is calculated and displayed. In addition, a time plot or pupil response curve appears automatically at the end of each measurement cycle. The plot for subsequent determinations replaces the previous curve and digital data are added beneath those of earlier cycles for easy comparison of successive data measurements. Pupil constriction velocity vs time plots may be printed directly without leaving the measurement mode or at the conclusion of a set of measurements. Saved measurement data may be recalled and additional measurements may be added to the file allowing comparison of current data with measurements from an earlier session, creation of a cumulative patient history, etc.

3. A Third Non-Invasive Apparatus: The PUPILSCREEN System

The S-7 device or PUPILSCREEN™ instrument is designed for convenient binocular measurements. A knob on the device quickly alternates the measurement from left to right eye.

The PUPILSCREEN™ devices are designed to automatically display pupil images and pupillary reflex graphs on a computer screen. Computer files are created which can be further manipulated by user programs or the optional spreadsheet analysis templates which we offer.

The S-7 instrument assembly functions on a plug-in accessory to an IBM PC or compatible personal computer; is operated by an easy-to-use, menu-driven, program, offering a range of programmable measurement variables; and provides for automatic storage of pupil measurement data as well as retrieval and analysis of subject data from a database for rapid comparisons with previous or baseline measurements. The S-7 device is a table-top instrument ideal for large volume screening tests in which the subject aligns his eyes with aid of a video image of the pupil. Once aligned, the subject himself presses a switch to initiate an automatic single or multiple cycle measurement sequence.

Once the eye to be measured is set by rotating the selector knob on the top of the unit, subject identification is entered from the computer keyboard in response to a screen prompt. The subject positions his head against the foam rubber face pad and fixes his gaze straight ahead where the pupil image will be displayed in the optical unit. The subject then initiates the measure cycle by pressing a switch. After each measurement cycle the computer monitor will display the pupil response curve and the key parameters of pupil size and response characteristics will appear on the monitor display.

Each additional measurement cycle will be recorded and displayed independently on the monitor.

We claim:

1. A non-invasive method for diagnosing the presence or absence of Alzheimer's disease in a living subject which comprises:
   a) administering to one of said subject's eyes at least one neural transmitter mediator in an amount insufficient to cause a significant pupil constriction or dilation if said subject is not afflicted with Alzheimer's disease,
   b) photostimulating said subject's treated eye with one or more episodes of visible light to induce pupillary constriction,
   c) repetitively and episodically measuring pupil diameter in said treated eye during said pupillary constriction in response to said photostimulation, and
   d) diagnosing the presence or absence of Alzheimer's disease in said subject based on the presence or absence of Alzheimer-characteristic pupil diameter changes from a baseline pupil diameter established for said treated eye or Alzheimer-characteristic pupil diameter rates of change calculated from said pupil diameter change measurements.

2. A method according to claim 1 wherein said repetitive and episodic measurements comprise at least 1000 measurements per episode of measurement.

3. A method according to claim 1 wherein said repetitive and episodic measurements comprise measurement of at least 50 Hertz during said constriction.

4. A method according to claim 2 or 3 wherein at least three episodes of measurement are taken.

5. A method according to claim 2 or 3 wherein said episodes of measurements extend timewise to at least a period of expected maximal pupillary response.

6. A method according to claim 1 wherein said neural transmitter mediator is a cholinergic antagonist.

7. A method according to claim 6 wherein said cholinergic antagonist is about 0.01% tropicamide.

8. A method according to claim 7 wherein said repetitive and episodic measurements comprise measurements at 60 Hertz over 30 seconds for each such episode and wherein at least five such episodes extend over at least 30 minutes.

9. A method according to claim 8 wherein the Alzheimer'-characteristic change in pupil diameter is at least a 13% change from the normal control group.

10. A non-invasive method for diagnosing Alzheimer's disease in a living human subject, said diagnostic method comprising the steps of:
    providing a non-invasive automated apparatus which can continuously monitor pupil diameter size over time, repetitively measure pupil diameter size over time for a prechosen duration ranging from about less than 1 second to about 5 minutes, and cumulatively record such monitored and measured pupil diameter size information as is obtained over time;
    identifying one eye in the living human subject as a targeted eye;
    using said non-invasive automated apparatus on a first measurement occasion to continuously monitor, repetitively measure, and cumulatively record the pupil diameter size of said targeted eye in the living human subject over the prechosen duration to provide primary information of pupil diameter size for said targeted eye;
    administering at least one neural transmitter mediator to said targeted eye of the living human subject in an amount insufficient to cause marked dilation of pupil diameter over time in a person not afflicted with Alzheimer's disease, said neural transmitter mediator being selected from the group consisting of cholinergic antagonists and adrenergic agonists;
    waiting a predetermined interval of time for said administered neural transmitter mediator to act upon said targeted eye; then
    using said non-invasive automated apparatus on at least a second measurement occasion to continuously monitor, repetitively measure, and cumulatively record the pupil diameter size of said targeted eye in the living human subject over the prechosen duration to provide secondary information of pupil diameter size for said targeted eye after being acted upon by said administered neural transmitter mediator; and
    determining such change in pupil diameter size for said targeted eye as may have occurred over said time interval by comparing said primary information with at least said secondary information, a marked increase in pupil diameter size for said targeted eye diagnostically establishing that living human subject as being afflicted with Alzheimer's disease.

11. The diagnostic method as recited in claim 10 wherein said neural transmitter mediator is an agent selected from the group consisting of tropicamide, atropine, homotropine hydrobromide, cyclopentolate hydrochloride, and scopolamine.

12. The diagnostic method as recited in claim 10 wherein said neural transmitter mediator is an agent selected from the group consisting of phenylephrine hydrochloride, hydroxyamphetamine hydrobromide, dipivefrin, and epinephrine.

13. The diagnostic method as recited in claim 10 wherein said neural transmitter mediator is a combination of cyclopentolate hydrochloride and phenylephrine.

14. A non-invasive method for diagnosing Alzheimer's disease in a living human subject, said diagnostic method comprising the steps of:
    providing a non-invasive automated apparatus which can continuously monitor pupil diameter size over time, repetitively measure pupil diameter size over time for a prechosen duration ranging from about less than 1 second to about 5 minutes, and cumulatively record such monitored and measured pupil diameter size information as obtained over time;
    identifying one eye in the living human subject as a targeted eye;
    using said non-invasive automated apparatus on a first measurement occasion to continuously monitor, repetitively measure, and cumulatively record the pupil diameter size of said targeted eye in the living human subject over the prechosen duration to provide primary information of pupil diameter size for said targeted eye;
    administering at least one neural transmitter mediator to said targeted eye of the living human subject in an amount insufficient to cause marked constriction of pupil diameter over time in a person not afflicted with Alzheimer's disease, said neural transmitter mediator being selected from the group consisting of cholinergic agonists and adrenergic antagonists;
    waiting a predetermined interval of time sufficient for said administered neural transmitter agonist to act upon said targeted eye; then
    using said non-invasive automated apparatus on at least a second measurement occasion to continuously monitor, repetitively measure, and cumulatively record the pupil diameter size of said targeted eye in the living human subject over the prechosen duration to provide secondary information of pupil diameter size for said targeted eye after being acted upon by said administered neural transmitter mediator; and determining such change in pupil diameter size for said targeted eye as may have occurred over said time interval by comparing said primary information with at least said secondary information, a marked decrease in pupil diameter size for said targeted eye diagnostically establishing that living human subject as being afflicted with Alzheimer's disease.

15. The diagnostic method as recited in claim 14 wherein said neural transmitter mediator is an agent selected from the group consisting of pilocarpine hydrochloride, pilocarpine nitrate, and carbachol.

16. The diagnostic method as recited in claim 14 wherein said neural transmitter mediator is an agent selected from the group consisting of physostigmine sulfate and physostigmine salicylate.

17. The diagnostic method as recited in claim 14 wherein said neural transmitter mediator is an agent selected from the group consisting of demecarium bromide and echothiophate iodide.

18. The diagnostic method as recited in claim 14 wherein said neural transmitter mediator is timolol maleate.

19. A non-invasive method for diagnosing Alzheimer's disease in a living human subject, said diagnostic method comprising the steps of:

providing a non-invasive automated apparatus which can continuously monitor pupil diameter size over time, repetitively measure pupil diameter size over time for a prechosen duration ranging from about less than 1 second to about 5 minutes, and cumulatively record such monitored and measured pupil diameter size information as is obtained over time;

identifying one eye in the living human subject as a targeted eye;

using said non-invasive automated apparatus on a first measurement occasion to continuously monitor, repetitively measure, and cumulatively record the pupil diameter size of said targeted eye in the living human subject over the prechosen duration to provide primary informational data of pupil diameter size for said targeted eye;

administering at least one neural transmitter mediator to said targeted eye of the living human subject in an amount insufficient to cause marked changes in pupil diameter over time in a person not afflicted with Alzheimer's disease, said neural transmitter mediator being selected from the group consisting of cholinergic agonists, cholinergic antagonists, adrenergic agonists, and adrenergic antagonists;

waiting a predetermined interval of time sufficient for said administered neural transmitter mediator to act upon said targeted eye; then using said non-invasive automated apparatus on at least a second measurement occasion subsequently to continuously monitor, repetitively measure, and cumulatively record the pupil diameter size of said targeted eye in the living human subject over the prechosen duration to provide at least secondary informational data of pupil diameter size for said targeted eye after being acted upon by said administered neural transmitter mediator; and determining the rate of pupil diameter change for said targeted eye as may have occurred over said time interval by comparing said primary informational data with at least said secondary informational data, a rapid rate of pupil diameter change for said targeted eye diagnostically establishing that living human subject as being afflicted with Alzheimer's disease.

* * * * *